(12) United States Patent
Sah et al.

(10) Patent No.: US 8,163,875 B2
(45) Date of Patent: Apr. 24, 2012

(54) POLYMER CONJUGATED GLYCOSYLATED NEUBLASTIN

(75) Inventors: Dinah Wen-Yee Sah, Boston, MA (US); R. Blake Pepinsky, Arlington, MA (US); Anthony Rossomando, South Grafton, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 1324 days.

(21) Appl. No.: 10/553,710

(22) PCT Filed: Apr. 16, 2004

(86) PCT No.: PCT/US2004/011745
§ 371 (c)(1),
(2), (4) Date: Feb. 27, 2007

(87) PCT Pub. No.: WO2004/094592
PCT Pub. Date: Nov. 4, 2004

(65) Prior Publication Data
US 2007/0238650 A1    Oct. 11, 2007

Related U.S. Application Data

(60) Provisional application No. 60/463,899, filed on Apr. 18, 2003.

(51) Int. Cl.
*A61K 38/18* (2006.01)
*A61K 38/00* (2006.01)

(52) U.S. Cl. ....... 530/350; 514/1.1; 514/17.7; 514/20.9; 514/7.5; 514/7.6; 514/8.3; 514/18.2; 514/18.3

(58) Field of Classification Search .................. None
See application file for complete search history.

(56) References Cited

U.S. PATENT DOCUMENTS

| | | | |
|---|---|---|---|
| 4,352,883 A | 10/1982 | Lim | |
| 4,353,888 A | 10/1982 | Sefton | |
| 4,407,957 A | 10/1983 | Lim | |
| 4,883,666 A | 11/1989 | Sabel et al. | |
| 4,968,733 A | 11/1990 | Muller et al. | |
| 4,976,859 A | 12/1990 | Wechs | |
| 5,084,350 A | 1/1992 | Chang et al. | |
| 5,158,881 A | 10/1992 | Aebischer et al. | |
| 5,194,596 A | 3/1993 | Tischer et al. | |
| 5,284,761 A | 2/1994 | Aebischer et al. | |
| 5,350,836 A | 9/1994 | Kopchick et al. | |
| 5,414,135 A | 5/1995 | Snow et al. | |
| 5,445,934 A | 8/1995 | Fodor et al. | |
| 5,496,804 A | 3/1996 | Reed et al. | |
| 5,525,464 A | 6/1996 | Drmanac et al. | |
| 5,618,531 A | 4/1997 | Cherksey | |
| 5,641,749 A | 6/1997 | Yan et al. | |
| 5,650,494 A | 7/1997 | Cerletti et al. | |
| 5,654,007 A | 8/1997 | Johnson et al. | |
| 5,733,729 A | 3/1998 | Lipshutz et al. | |
| 5,754,524 A | 5/1998 | Wark | |
| 5,770,577 A | 6/1998 | Kinstler et al. | |
| 5,775,320 A | 7/1998 | Patton et al. | |
| 5,780,014 A | 7/1998 | Eljamal et al. | |
| 5,780,019 A | 7/1998 | Klier et al. | |
| 5,785,049 A | 7/1998 | Smith et al. | |
| 5,795,716 A | 8/1998 | Chee et al. | |
| 5,798,113 A | 8/1998 | Dionne et al. | |
| 5,800,992 A | 9/1998 | Fodor et al. | |
| 5,814,607 A | 9/1998 | Patton | |
| 5,834,029 A | 11/1998 | Bellamkonda et al. | |
| 5,846,935 A | 12/1998 | Panayotatos | |
| 5,916,555 A | 6/1999 | Lee et al. | |
| 5,939,524 A | 8/1999 | Bowditch et al. | |
| 6,063,757 A | 5/2000 | Urso | |
| 6,083,725 A | 7/2000 | Selden et al. | |
| 6,084,076 A | 7/2000 | Ejima et al. | |
| 6,284,540 B1 | 9/2001 | Milbrandt et al. | |
| 6,299,895 B1 | 10/2001 | Hammang et al. | |
| 6,361,771 B1 | 3/2002 | Tao et al. | |
| 6,593,133 B1 | 7/2003 | Johansen et al. | |
| 6,677,135 B1 | 1/2004 | Sanicola-Nadel et al. | |
| 6,723,344 B2 | 4/2004 | Sakiyama-Elbert et al. | |
| 6,734,284 B1 | 5/2004 | Johansen et al. | |
| 7,067,473 B1 | 6/2006 | Masure | |
| 7,115,257 B1 | 10/2006 | Tao et al. | |
| 7,276,580 B2 | 10/2007 | Sah et al. | |
| 7,358,228 B2 | 4/2008 | Sah et al. | |
| 7,442,370 B2 | 10/2008 | Sah et al. | |
| 7,598,059 B2 | 10/2009 | Pederson et al. | |
| 7,601,518 B2 | 10/2009 | Wahlberg et al. | |
| 7,655,463 B2 | 2/2010 | Sah et al. | |
| 2002/0002269 A1 | 1/2002 | Milbrandt et al. | |
| 2002/0055467 A1 | 5/2002 | Johansen et al. | |
| 2002/0114780 A1 | 8/2002 | Bankiewicz et al. | |
| 2003/0078373 A1 | 4/2003 | Fersht et al. | |
| 2003/0100497 A1 | 5/2003 | Baker et al. | |
| 2003/0166537 A1 | 9/2003 | Hanke | |

(Continued)

FOREIGN PATENT DOCUMENTS

EP    1 373 503    11/2007

(Continued)

OTHER PUBLICATIONS

Abrams et al., "Emerging strategies to promote improved functional outcome after peripheral nerve injury," Restor. Neurol. Neurosci., 23(5-6):367-82 (2005).

(Continued)

*Primary Examiner* — Daniel C Gamett
(74) *Attorney, Agent, or Firm* — Fish & Richardson P.C.

(57) ABSTRACT

The following class of molecule is disclosed: a dimer containing a first neublastin polypeptide and a second neublastin polypeptide, wherein: (a) at least one of the polypeptides is glycosylated; (b) at least one of the polypeptides is conjugated at its N-terminus to a water-soluble synthetic polymer; and (c) neither of the polypeptides is conjugated to a water-soluble synthetic polymer at a position other than the N-terminus. Such dimers possess the biological activity of wild-type neublastin while displaying enhanced serum half-life and enhanced potency relative to wild-type neublastin.

48 Claims, 6 Drawing Sheets

U.S. PATENT DOCUMENTS

| | | | |
|---|---|---|---|
| 2003/0186267 A1 | 10/2003 | Feder et al. |
| 2004/0028613 A1 | 2/2004 | Quay |
| 2004/0077543 A1 | 4/2004 | Sah et al. |
| 2004/0142418 A1 | 7/2004 | Sah et al. |
| 2004/0230043 A1 | 11/2004 | Johansen et al. |
| 2004/0242472 A1 | 12/2004 | Shelton et al. |
| 2004/0265972 A1 | 12/2004 | Weintraub et al. |
| 2005/0069520 A1 | 3/2005 | Shi et al. |
| 2005/0089960 A1 | 4/2005 | Wahlberg et al. |
| 2005/0118157 A1 | 6/2005 | McMahon et al. |
| 2005/0142098 A1 | 6/2005 | Sah et al. |
| 2005/0158824 A1 | 7/2005 | Pedersen et al. |
| 2005/0180957 A1 | 8/2005 | Scharp et al. |
| 2005/0181991 A1 | 8/2005 | Shelton et al. |
| 2005/0233359 A1 | 10/2005 | Masure et al. |
| 2006/0009625 A1 | 1/2006 | Bedows et al. |
| 2006/0014288 A1 | 1/2006 | Kim et al. |
| 2006/0122135 A1 | 6/2006 | Geerts et al. |
| 2007/0238650 A1 | 10/2007 | Sah et al. |
| 2007/0254842 A1 | 11/2007 | Bankiewicz |
| 2008/0039385 A1 | 2/2008 | Rossomando et al. |
| 2008/0227703 A1 | 9/2008 | Johansen et al. |
| 2008/0249287 A1 | 10/2008 | Rossomando et al. |
| 2008/0260702 A1 | 10/2008 | Jorgensen |
| 2008/0306212 A1 | 12/2008 | Sah et al. |
| 2009/0221495 A1 | 9/2009 | Rossomando et al. |
| 2009/0258831 A1 | 10/2009 | Sah |
| 2010/0056440 A1 | 3/2010 | Rossomando et al. |
| 2010/0234293 A1 | 9/2010 | Johansen et al. |
| 2010/0261654 A1 | 10/2010 | Rossomando et al. |
| 2010/0292142 A1 | 11/2010 | Sah et al. |

FOREIGN PATENT DOCUMENTS

| | | |
|---|---|---|
| EP | 1 930 439 | 6/2008 |
| JP | 11-310600 | 11/1999 |
| JP | 2002-534957 | 10/2002 |
| JP | 2003-310258 | 11/2003 |
| RU | 2225728 | 8/1999 |
| WO | WO 92/19195 | 11/1992 |
| WO | WO 93/06116 | 4/1993 |
| WO | WO 95/05452 | 2/1995 |
| WO | WO 97/08196 | 3/1997 |
| WO | WO 97/11964 | 4/1997 |
| WO | WO 97/19693 | 6/1997 |
| WO | WO 98/32869 | 7/1998 |
| WO | WO 99/03887 | 1/1999 |
| WO | WO 99/13090 | 3/1999 |
| WO | WO 99/42486 | 8/1999 |
| WO | WO 99/43813 | 9/1999 |
| WO | WO 99/49039 | 9/1999 |
| WO | WO 00/01815 | 1/2000 |
| WO | WO 00/04050 | 1/2000 |
| WO | WO 00/15665 | 3/2000 |
| WO | WO 00/17360 | 3/2000 |
| WO | WO 00/18799 | 4/2000 |
| WO | WO 00/34475 | 6/2000 |
| WO | WO 00/73348 | 12/2000 |
| WO | WO 01/47946 | 7/2001 |
| WO | WO 01/53486 | 7/2001 |
| WO | WO 01/66164 | 9/2001 |
| WO | WO 01/76639 | 10/2001 |
| WO | WO 01/87925 | 11/2001 |
| WO | WO 02/46430 | 6/2002 |
| WO | WO 02/051433 | 7/2002 |
| WO | WO 02/060929 | 8/2002 |
| WO | WO 02/072826 | 9/2002 |
| WO | WO 02/078730 | 10/2002 |
| WO | WO 03/044055 | 5/2003 |
| WO | WO 2004/002763 | 1/2004 |
| WO | WO 2004/069176 | 8/2004 |
| WO | WO 2004/094592 | 11/2004 |
| WO | WO 2004/108760 | 12/2004 |
| WO | WO 2005/039643 | 5/2005 |
| WO | WO 2006/023781 | 3/2006 |
| WO | WO 2006/023782 | 3/2006 |
| WO | WO 2007/042040 | 4/2007 |
| WO | WO 2007/100898 | 9/2007 |
| WO | WO 2007/103182 | 9/2007 |
| WO | WO 2008/137574 | 11/2008 |
| WO | WO 2009/020964 | 2/2009 |

OTHER PUBLICATIONS

Aebischer et al, "Recombinant proteins for neurodegenerative diseases: the delivery issue," Trends in Neuroscience, Elsevier, Amsterdam, NL 24(9):533-540 (2001).

Aebischer et al., "Intrathecal delivery of CNTF using encapsulated genetically modified xenogeneic cells in amyotrophic lateral sclerosis patients," Nature Medicine, 2:696-699 (1996).

Airaksinen et al., GDNF family neurotrophic factor signaling: four masters, one servant, Mol. Cell Neurosci., 13:313-325 (1999).

Airaksinen et al., "The GDNF family: signalling, biological functions and therapeutic value," Nature Reviews, Neuroscience 3:383-394 (May 2002).

Alfano et al., "The major determinant of the heparin binding of glial cell-line-derived neurotrophic factor is near the N-terminus and is dispensable for receptor binding," Biochem. J., 404(1):131-40 (2007).

Algvere et al., "Transplantation of RPE in age-related macular degeneration: observations in disciform lesions and dry RPE atrophy," Graefe's Arch. Clin. Exp. Ophthalmol., 235:149-158 (1997).

Anderson, "Human gene therapy," Nature, 392:25-30 (1998).

Andres et al., "Multiple effects of artemin on sympathetic neurone generation, survival and growth," Development 128:3685-3695 (2001).

Anonymous, "Anti-human Artemin Antibody," R&D Systems Product Data Sheets (Dec. 27, 2006), [online] XP002505114. Retrieved from the Internet: http://www.rndsystems.com/pdf/AF2589.pdf [retrieved on Nov. 21, 2008].

Anonymous, "Monoclonal Anti-human Artemin Antibody," R&D Systems Product Data Sheets (Mar. 23, 2006), [online] XP002505115. Retrieved from the Internet: http://www.rndsystems.com/pdf/MAB2589.pdf [retrieved on Nov. 21, 2008].

Atschul et al., "Gapped BLAST and PSI-BLAST: a new generation of protein database search programs," Nucl. Acids Res., 25:3389-3402 (1997).

Baloh et al. "Artemin, a novel member of the GDNF ligand family, supports peripheral and central neurons and signals through the GFRalpha3-RET receptor complex," Neuron, 21(6):1291-1302 (1998).

Baloh et al., "Functional mapping of receptor specificity domains of glial cell line-derived neurothropic factor (GDNF) family ligands and production of GFR alpha 1 RET-specific agonists," J. of Biological Chemistry, 275(5):3412-3420 (2000).

Baudet et al., "Positive and negative interactions of GDNF, NTN and ART in developing sensory neuron subpopulations, and their collaboration with neurotrophins," Development, 127:4335-4344 (2000).

Bauskin et al., "The propeptide of macrophage inhibitory cytokine (MIC-1), a TGF-β superfamily member, acts as a quality control determinant for correctly folded MIC-1," The EMBO Journal, 19(10):2212-2220 (2000).

Bendtsen et al., "Improved prediction of signal peptides—SignalP 3.0," J. Mol. Biol., 340(4):783-795 (2004).

Bennett et al., "Artemin has potent neurotrophic actions on injured C-fibres," J. Peripher. Nerv. Syst., 11(4):330-45 (2006).

Bennett et al., "A distinct subgroup of small DRG cells express GDNF receptor components and GDNF is protective for these neurons after nerve injury," J. Neurosci. 18(8):3059-3072 (Apr. 15, 1998).

Bennett, G., "An animal model of neuropathic pain: A review," Muscle & Nerve 16:1040-1048 (1993).

Bonde et al., "GDNF and neublastin protect against NMDA-induced excitotoxicity in hipocampal slice cultures," Neuroreport., 11:4069-4073 (2000).

Bootcov et al., "MIC-1, a novel macrophage inhibitory cytokine, is a divergent member of the TGF-β superfamily," Pro. Natl. Acad. Sci. U.S.A., 94:11514-11519 (1997).

Bork, "Go hunting in sequence databases but watch out of the traps," Trends in Genetics, 12:425-427 (1996).

Bork, "Powers and Pitfalls in Sequence analysis: the 70% Hurdle," Genome Research, 10:398-400 (2000).
Borodovsky et al., "Detection of new genes in a bacterial genome using Markov models for three gene classes," Nucl. Acids Res., 23:3554-3562 (1995).
Boucher et al "Artemin prevents injury-induced changes in small sensory neurons," Abstracts of the Society for Neuroscience, Society for Neuroscience, Washington D.C. 26(1/2):63305 (2000).
Brenner, "Errors in genome annotation," Trends in Genetics, 15:132-133 (1999).
Burgess et al., "Possible dissociation of the heparin-binding and mitogenic activities of heparin-binding (acidic fibroblast) growth factor-1 from its receptor-binding activities by site-directed mutagenesis of a single lysine residue," J. of Cell Biology, 111:2129-2138 (1990).
Callister et al., Soc. For Neuroscience Abstracts 27(1):36.11 (2001).
Campbell et al., "Mechanisms of Neuropathic Pain," Neuron, 52:77-92 (2006).
Carmillo et al., "Glial Cell Line-Derived Neurotrophic Factor (GDNF) Receptor α-1(GFRα1) Is Highly Selective for GDNF versus Artemin," Biochemistry, 44:2545-2554 (2005).
Ceyhan et al., "The neurotrophic factor artemin promotes pancreatic cancer invasion," Ann. Surg., 244:274-81 (2006).
Ceyhan et al., "The neurotrophic factor artemin influences the extent of neural damage and growth in chronic pancreatitis," Gut., 56(4):534-44 (2007).
Damon et al., "Vascular-derived artemin: a determinant of vascular sympathetic innervation?," Am. J. Physiol. Heart Circ. Physiol., 293:H266-H273 (2007).
Daopin et al., "Crystal structure of TGF-J2 refined at 1.8 A resolution," Proteins, 17:176-192 (1993).
Delgado et al., "The uses and properties of PEG-Linked proteins," Critical Reviews in Therapeutic Drug Carrier Systems, 9(3/4):249-304 (1992).
Doerks et al., "Protein annotation: detective work for function prediction," Trends in Genetics, 14:248-250 (1998).
During et al., "Towards gene therapy for the central nervous system," Mol. Med., 11:485-493 (1998).
Eigenbrot et al., "X-ray structure of glial cell-derived neurotrophic factor at 1 9 A resolution and implications for receptor binding," Nat. Struct. Biol., 4:435-438 (1997).
Enomoto et al., "RET signaling is essential for migration, axonal growth and axon guidance of developing sympathetic neurons," Development, 128:3963-3974 (2001).
Enzmann et al., "Immunological problems of transplantation into the subretinal space," Acta Anat., 162:178-183 (1998).
Fairlie et al., "The propeptide of the transforming growth factor-β superfamily member, macrophage inhibitory cytokine-1 (MIC-1), is a multifunctional domain that can facilitate protein folding and secretion," J. of Biol. Chem., 276(20):16911-16918 (2001).
Finsen et al., "Somatostatin and neuropeptide Y in organotypic slice cultures of the rat hippocampus: an immunocytochemical and in situ hybridization study," Neurosci., 47:105-113 (1992).
Fjord-Larsen, et al. "Efficient in vivo protection of nigral dopaminergic neurons by lentiviral gene transfer of a modified Neurturin construct," Experimental Neurology, 195:49-60 (2005).
Flanders et al., "TGFβ," Laboratory of Cell Regulation and Carcinogenesis, National Cancer Institute, 719-746 (undated).
Francis et al., "Pegylation of Cytokines and other therapeutic proteins and peptides: the importance of biological optimization of coupling techniques," Int'l. Journal of Hematology, Elsevier Science Publishers, NL., 68(1):1-18 (1998).
Frankel et al., "High-Level Expression and Purifcation of the Recombinant Diphtheria Fusion Toxin DTGM for PHASE I Clinical Trials," Expr Purif. 16(1):190-201, (Jun. 1999).
Freynhagen et al., "The evaluation of neuropathic components in law back pain," Current Pain & Headache Reports 13:185-190 (2009).
Friedmann, "Principles for human gene therapy studies," Science, 287:2163-2164 (2000).
Gardell et al., "Multiple actions of systemic artemin in experimental neuropathy," Nat Med., 9(11):1383-89 (2003).
GenBank Accession No. AA844072, 2 pages (1998).
GenBank Accession No. AC005037, Waterston, 54 pages (1998).
GenBank Accession No. AC005038, Sulston et al., 96 pages (2001).
GenBank Accession No. AC005051, Waterston, 38 pages (1998).
GenBank Accession No. AF040962, Milbrandt et al., 2 pages (1998).
Genbank Accession No. AF120274, Rosenblad et al., 3 pages (1999).
Gilchuk, "Assessment of renaturation methods for industrial producing recombinant proteins in biologically active form from E.coli inclusion bodies," Biopolymers and Cell, 20(3):182-192 (2004).
Griffin et al., "Assessment of cutaneous innervation by skin biopsies," Current Opinion in Neurology, 14:655-659 (2001).
Guerra et al., "PEGylation prevents the N-terminal degradation of megakaryocyte growth and development factor," Pharm. Res., 15(12):1822-1827 (1998).
Gustafsson, "New insights in oestrogen receptor (ER) research—the ERbeta," Eur. J. Cancer, 36 Suppl. 4:S16 (2000).
Hall et al., "Eukaryotic and Prokaryotic Signal Peptides Direct Secretion of a Bacterial Endoglucanase by Mammalian Cells," Journal of Biological Chemistry, 265(32):19996-19999 (1990).
Hallböök et al., "Expression of Neurotrophins and Trk Receptors in the Avian Retina," J. Compar. Neurol., 364:664-676 (1996).
Hamilton et al., "Heparin coinfusion during convection-enhanced delivery (CED) increases the distribution of the glial-derived neurotrophic factor (GDNF) ligand family in rat striatum and enhances the pharmacological activity of neurturin," Experimental Neurology, 168:155-161 (2001).
Hoane et al. "Mammalian-Cell-Produced Neurturin (NTN) Is More Potent Than Purified Escherichia coli-Produced NTN," Exp. Neurol., 162:189-193 (2000).
Israel et al., "Acetylcholine Release and the Cholinergic Genomic Locus," Molecular Neurobio., 16(1):1-20 (1998).
Johansen et al., "Biosynthesis of peptide precursors and protease inhibitors using new consititutive and inducible eukaryotic expression vectors," FEBS Lett., 267:289-294 (1990).
Kim et al., "An experimental model for peripheral neuropathy produced by segmental spinal nerve ligation in the rat," Pain, 50:355-363 (1992).
Kirsch et al. "Expression of ciliary neurotrophic factor receptor mRNA and protein in the early postnatal and adult rat nervous system," Neurosci. Lett., 180:163-166 (1994).
Kotzbauer et al., "Neurturin, a relative of glial-cell-line-derived neurotrophic factor," Nature, 384:467-70 (1996).
Kron et al., "Coronary revascularization rather than cardiac transplantation for chronic ischemic cardiomyopathy," Ann. Surg., 210:348-352 (1989).
Lapchak et al., "Pharmacological characterization of glial cell line-derived neurotrophic factor (GDNF): implications for GDNF as a therapeutic molecule for treating neurodegenerative diseases," Cell Tissue Res., 286:179-189 (1996).
Lapchak, "Therapeutic potential for glial cell line-derived neurotropic factor (GDNF) based upon pharmacological activities in the CNS," Rev. Neurosci., 7:165-176 (1977).
Lavail et al., "Protection of mouse photoreceptors by survival factors in retinal degenerations," Invest. Ophthalmol. Vis. Sci., 39(3):592-602 (1998).
Lee et al., "Proliferin Secreted by Cultured Cells Binds to Mannose 6-Phosphate", J. Biol. Chem., 263(7):3521-3527 (1988).
Lee et al., "Prolonged circulating lives of single-chain Fv proteins conjugated with polyethylene glycol: a comparison of conjugation chemistries and compounds," Bioconjug. Chem., 10:973-981 (1999).
Li et al., "Beta-Endorphin omission analogs: dissociation of immunoreactivity from other biological activities," PNAS, 77(6):3211-14 (1980).
Li et al., "Expression, purification, and characterization of recombinant human neurturin secreted from the yeast Pichia pastoris," Protein Expression and Purification, 30(1):11-17 (2003).
Lin et al., "GDNF: a glial cell line-derived neurotrophic factor for midbrain dopaminergic neurons," Science, 260:1130-1132 (1993).
Little et al., "Transplantation of human fetal retinal pigment epithelium rescues photoreceptor cells from degeneration in the royal college of surgeons rat retina," Invest. Ophthalmol. Vis. Sci., 37(1):204-211 (1996).
Lorenz et al., "Heteromultimeric CLC chloride channels with novel properties," Proc. Natl. Acad. Sci USA, 93:13362-13366 (1996).

Machelska et al., "Breaking the pain barrier," Nature Medicine 9(11):1353-1354 (2003).
Maeda et al., "Efficient Production of Active TNF I By albumin Signal Peptide," Biochemistry and Molecular Biology International, Academic Press, London, GB, 42(4):825-832 (1997).
Massague et al., "The TGF-J family and its composite receptor," Trends Cell Biol., 4:172-178 (1994).
Mason, "The RET receptor tyrosine kinase: activation, signalling and significance in neural development and disease," Pharm. Acta. Helv., 74:261-4 (2000).
Masure et al., "Enovin, a novel member of the GDNF family of neurotrophic growth factors with growth promoting and neuroprotective effects on neuronal cells," a poster presentation from Janssen Research Foundation, "Gordon Conference" held on Jun. 6-11, 1999.
Masure, et al., "Enovin, a member of the glial cell-line-derived neurotrophic factor (GDNF) family with growth promoting activity on neuronal cells," Eur J. Biochem., 266:892-902 (1999).
Masure et al., "Mammalian GFRalpha -4, a divergent member of the GFRalpha family of coreceptors for glial cell line-derived neurotrophic factor family ligands, is a receptor for the neurotrophic factor persephin," J. Biol. Chem., 275:39427-34 (2000).
Matsushita et al., "Cloning and structural organization of the gene encoding the mouse glial cell line-derived neurotrophic factor, GDNF," Gene, 203:149-157 (1997).
McDonald et al., "A structural superfamily of growth factors containing a cystine knot motif.," Cell, 73:421-424 (1993).
Merlo et al. "The Mouse int-2 Gene Exhibits Basic Fribroblast Growth Facctor Activity in a Basic Fibroblast Growth Factor-responsive Cell Line," Cell Growth & Differentiation, 1:463-472 (1990).
Milbrandt et al., "Persephin, a novel neurotrophic factor related to GDNF and Neurturin," Neuron, 20:245-253 (1998).
Mogyoros et al., "Strength-duration properties of sensory and motor axons in amyotrophic lateral sclerosis," Brain 121:851-859 (1998).
Moore et al., "Renal and neuronal abnormalities in mice lacking GDNF," Nature, 382:76-79 (1996).
Moustakas et al., "Smad regulation in TGF-$\beta$ signal transduction," J. of Cell Science, 114:4359-4369 (2001).
Ngo et al., "The Protein Folding Problem and Tertiary Structure Prediction," Birkhäuser, 492-495 (1994).
Nielsen et al., "Identification of prokaryotic and eukaryotic signal peptides and prediction of their cleavage sites," Protein Engineering, 10(1):1-6 (1997).
Nielsen et al., "Prediction of signal peptides and signal anchors by a hidden Markov model," Proceedings of the 6th International Conference on Intelligent systems for Molecular Biology, 122-130 (1998).
Nishino et al., "GFR alpha3, a component of the artemin receptor, is required for migration and survival of the superior cervical ganglion," Neuron, 23(4):725-736 (1999).
Norton et al., "Bacterial beta-Galactosidase as a Marker of Rous Sarcoma Virus Gene Expression and Replication," Mol. Cell. Biol., 5:281-290 (1985).
Orozco et al., "Nociceptive Neurons Express GFR$\alpha$3," Society for Neuroscience, Abstracts 26 (1-2): Abstract No. 412.7 (2000).
Orozco et al., "GFRalpha3 is expressed predominantly in nociceptive sensory neurons," Eur. J. Neurosci., 13(11):2177-82 (2001).
Palmiter, "Heterologous introns can enhance expression of transgenes in mice," PNAS, 88:478-482 (1991).
Park et al., "Coordinated interaction of the vascular and nervous systems: from molecule- to cell-based approaches," Biochem. Biophys. Res. Commun., 311:247-253 (311) (2003).
Park et al., "Tarnscriptional regulation of artemin is related to neurite outgrowth and actin polymerization in mature DRG neurons," Neuroscience Letters 404:61-66 (2006).
Pawson et al., "Assembly of cell regulatory systems through protein interaction domains," Science, 300:445-452 (2003).
PIR_80 Accession No. 14968.
Pons et al., "Massive cortical reorganization after sensory deafferentation in adult macaques," Scient. 252(5014):1857-1860 (1991).
Rakowicz et al., "Glial Cell Line-Derived Neurotrophic Factor Promotes the Survival of Early Postnatal Spinal Motor Neurons in the Lateral and Medial Motor Columns in Slice Culture," The Journal of Neuroscience, 22(10):3953-3962 (2002).
Ramachandran et al., "Perceptual correlates of massive cortical reorganization," Science 258(5085):1159-1160 (1992).
Ramachandran, "Behavioral and MEG correlates of neural plasticity in the adult human brain," Proceedings of the National Academy of Sciences 90:10413-10420 (1993).
Ramer et al., "Functional regeneration of sensory axons into the adult spinal cord," Nature 403:312-316 (Jan. 2000).
Rattenholl et al., "Pro-sequence assisted folding and disulfide bond formation of human nerve growth factor," J. Mol. Biol., 305:523-533 (2001).
Rattenholl et al., "The pro-sequence facilitates folding of human nerve growth factor from *Escherichia coli* inclusion bodies," Eur. J. Biochem., 268:3296-3303 (2001).
Reddy, "Controlled-release peylation, liposomal formulations: new mechanisms in the delivery of injectable drugs," Annals of Pharmacotherapy, 34(7/8):915-923 (2000).
Reinshagen et al., "Commercial recombinant human $\beta$-Nerve Growth factor and adult rat dorsal root ganglia contain an identical molecular species of nerve growth factor prohormone," J. of Neurochemistry, 74:2127-2133 (2000).
Rico et al., "Characterization of the immunostimulatory properties of Leishmania infantum HSP70 by fusion to the *Escherichia coli* maltose-binding protein in normal and nu/nu BALB/c mice," Infect Immun. 66:1347-352 (Jan. 1998).
Riganti et al., "Nitroarginine methyl ester and canavanine lower intracellular reduced glutathione," Free Radic. Biol. Med., 35(10):1210-6 (2003).
Robertson et al., "The GDNF-RET signaling in partnership," Trends Genet., 13:1-3 (1997).
Rosenberg et al., "Gene therapist, heal thyself," Science, 287:1751 (2000).
Rosenberg et al., "Vectors for selective expression of cloned DNAs by T7 RNA polymerase," Gene, 56:125-135 (1987).
Rosenblad et al., "In vivo protection of nigral dopamine neurons by lentiviral gene transfer of the novel GDNF-family member neublastin/artemin," Molecular and Cellular Neuroscience, 15(2):199-214 (2000).
Rosenblad et al., "In vivo protection of nigral dopamine neurons by lentiviral gene transfer of the novel GDNF-family member neublastin/artemin," Mol. Cell Neurosci., 18(3):332-333 (2001).
Rossomando et al., "In vitro and in vivo characterization of neublastin, a nociceptive neuronal trophic factor," Abstracts of the Annual Meeting of the Society for Neuroscience, Society for Neuroscience, Washington, DC, U.S., 27(1):361 (2001) (XP001121851, ISSN: 0190-5295).
Saarma et al., "Other neurotrophic factors: glial cell line-derived neurotrophic factor (GDNF)," Microsc. Res. Tech., 45(4-5):292-302 (1999).
Saarma, "GDNF: A stranger in the TGF-beta superfamily?" European Journal of Biochemistry, 267(24):6968-6971 (2000).
Sadick et al., "Analysis of hereguljn-induced ErbB2 phosphorylation with a high-throughput Kinase receptor activation enzyme-linked immunosorbant assay," Anal. Biochem., 235(2):207-14 (1996).
Sah et al., "Prevention and Reversal of Experimental Neuropathic Pain by Systemic Neublastin," Society for Neuroscience Abstracts, 27(1):361 (2001).
Sah et al., "Neurotrophic factors as novel therapeutics for neuropathic pain," Nature Reviews 2:460-472 (2003).
Sah et al., "New approaches for the treatment of pain: the GDNF family of neurotrophic growth factors," Curr. Top Med. Chem., 5(6):577-83 (2005).
Sanicola et al., "Glial cell line-derived neurotrophic factor-dependent RET activation can be mediated by two different cell-surface accessory proteins," Proc Natl Acad Sci, USA, 94:6238-6243 (1997).
Sauer et al., "Progressive degeneration of nigrostriatal dopamine neurons following intrastraiatal terminal lesions with 6-hydroxydopamine: a combined retrograde tracing and immunocytochemical study in the rat," Neuroscience, 59:401-415 (1994).
Schmidt et al. "In vivo kinetics as a sensitive method for testing physiologically intact human recombinant apolipoprotein A-1: comparison of three different expression systems," Clinica Chimica Acta, 268(1-2):41-60 (1997).

Silvian, L. et al., "Artemin crystal structure reveals insights into heparan sulfate binding," Biochemistry 45(22):6801-12 (Jun. 2006).
Skolnick et al. "From genes to protein structure and function: novel applications of computational approaches in the genomic era," Trends in Biotech, 18(1):34-39 (2000).
Sloot et al., "Detection of salicylate and its hydroxylated adducts 2.3- and 2.5-dihydroxybenzoic acids as possible indices for in vivo hydroxyl radical formation in combination with catechol- and indoleamines and their metabolites in cerebrospinal fluid and brain tissue," J. Neurosci. Meth., 60:141-149 (1995).
Smith et al. "The challenges of genome sequence annotation" or "The devil is in the details," Nature Biotechnology, 15:1222-1223 (1997).
Snider et al., "Tackling pain at the source: new ideas about nociceptors," Neuron 20:629-632 (Apr. 1998).
Stoppini et al., "A simple method for organotypic cultures of nervous tissue," J. Neurosci. Methods, 37:173-182 (1991).
Thompson et al., "The ClustalX windows interface: flexible strategies for multiple sequence alignment aided by quality analysis tools," Nucl. Acids Res., 25:4876-4882 (1997).
Trupp et al., "Peripheral expression and biological ctivities of GDNF, a new neurotrophic factor for avian and mammalian peripheral neurons," The Journal of Cell Biology 130(1):137-148 (Jul. 1995).
Tseng et al., "Neurturin protects dopaminergic neurons following medial forebrain bundle axotomy," Mol. Neurosci, 9:1817-1822 (1998).
Unsicker, "GDNF: a cytokine at the interface of TGF-betas and neurotrophins," Cell Tissue Res., 286:175-178 (1996).
Vallejo et al., "Optimized procedure for renaturation of recombinant human bone morphogenetic protein-2 at high protein concentration," Biotechnol. Bioeng., 85(6):601-609 (2004).
Varmus, "Gene therapy: Not ready for prime time," Nature Medicine, 2(1):7-8 (1996).
Verma et al., "Gene therapy-promises, problems and prospects," Nature, 389:239-242 (1997).
Verma, "Gene therapy: beyond 2000," Mol. Ther., 6:493 (2000).
Veronese et al., "Introduction and Overview of Peptide and Protein Pegylation," Advanced Drug Delivery Reviews, 54(4):453-456 (2002).
Vickers, "A vaccine against Alzheimer's disease: developments to date." Drugs Aging 19(7):487-94 (2002).
Von Schwedler et al., "Vif is crucial for human immunodeficiency virus type 1 proviral DNA synthesis in infected cells," J. Virol., 67:4945-4955 (1993).
Vukicevic et al., "Induction of nephrogenic mesenchyme by osteogenic protein 1 (bone morphogenetic protein 7)," PNAS USA, 93:9021-9026 (1996).
Wang et al., "Single-chain Fv with manifold N-glycans as bifunctional scaffolds for immunomolecules," Protein Eng., 11(12):1277-83 (1998).
Wang et al., "Animal and cellular models of chronic pain ," Adv. Drug Delivery Rev., 55:949-965 (2003).
Wang et al , "Inhibitory effect of endostatin expressed by human liver carcinoma SMMC7721 on endothelial cell proliferation in vitro," World Journal of Gastroenterology, 8(2):253-257 (2002).
Wang et al., "Persistent Restoration of sensory function by immediate or delayed systemic artemin after dorsal root injury," Nature Neurosci. 11(4):488-496 (2008).
Watabe et al., "Spontaneously immortalized adult mouse Schwann cells secrete autocrine and paracrine growth-promoting activities," J. Neurosci. Res., 41:279-90 (1995).
Wefstaedt et al., "Neurotrophic factors of the GDNF family and their receptors are detectable in spiral ganglion cells of normal hearing as well as of deafened rats," Laryngorhinootologie, 85(11):802-8 (2006) (English abstract only, see p. 807).
Wells, "Additivity of Mutational Effects in Proteins," Biochemistry, 29:8509-8517 (1990).
West et al., "Estimation of the Number of Somatostatin Neurons in the Striatum: An In Situ Hybridization Study Using the Optical Fractionator Method," J. Comp. Neurol., 370:11-22 (1996).
White et al., "Chemokines: integrators of pain and inflammation," Nat Rev. Drug discovery 4:834-844 (2005).
Yan, M. et al., "Two-amino acid molecular switch in an epithelial morphogen that regulates binding to two distinct receptors," Science 290:523-527 (2000).
Zufferey et al., "Multiply attenuated lentiviral vector achieves efficient gene delivery in vivo," Nat. Biotechnol., 15:871-875 (1997).
Accession No. AF109402 (1998).
Honma et al., "Artemin is a vascular-derived neurotrophic factor for developing sympathetic neurons," Neuron 35(2):267-282 (2002).
Mills, C.D. et al., "Strain and model differences in behavioral outcomes after spinal cord injury in rat," J. Neurotrauma 18(8):743-56, 2001.
Purves, D. et al.; "The Cover, Dorsal view of the human brain," Neuroscience, Sinauer Associates, Inc., 2nd Ed., pp. 75, 367, 400, 403, 554, 555, and 678, 2001.
Stokes, B.T. et al., "Experimental modeling of human spinal cord injury: a model that crosses the species barrier and mimics the spectrum of human cytopathology," Spinal Cord 49:101-109, 2002.
Talac, R. et al., "Animal models of spinal cord injury for evaluation of tissue engineering treatment strategies," Biomaterials 25:1505-1510, 2004.

FIG. 3

| | | |
|---|---|---|
| 1 | AGGPGSRARAAGARGCRLRSQLVPVRALGLGHRSDELVRF | human |
| | AGTRSSRARTTDARGCRLRSQLVPVSALGLGHSSDELIRF | mouse |
| | AGTRSSRARATDARGCRLRSQLVPVSALGLGHSSDELIRF | rat |
| | ||   ||||    ||||||||||||| |||||| |||| || | |
| | ag---srar---argcrlrsqlvpv-alglgh-sdel-rf | consensus |
| | | |
| 41 | RFCSGSCRRARSPHDLSLASLLGAGALRPPPGSRPVSQPC | human |
| | RFCSGSCRRARSQHDLSLASLLGAGALRSPPGSRPISQPC | mouse |
| | RFCSGSCRRARSPHDLSLASLLGAGALRSPPGSRPISQPC | rat |
| | ||||||||||||||||||||||||||||||||||||||| | |
| | rfcsgscrrars-hdlslasllgagalr-ppgsrp-sqpc | consensus |
| | | |
| 81 | CRPTRYEAVSFMDVNSTWRTVDRLSATACGCLG | human (SEQ ID NO:2) |
| | CRPTRYEAVSFMDVNSTWRTVDHLSATACGCLG | mouse (SEQ ID NO:3) |
| | CRPTRYEAVSFMDVNSTWRTVDHLSATACGCLG | rat   (SEQ ID NO:4) |
| | |||||||||||||||||||||||| |||||||| | |
| | crptryeavsfmdvnstwrtvd-lsatacgclg | consensus (SEQ ID NO:1) |
| | * | * = Asn95 |

FIG. 4

Consensus sequence: (SEQ ID NO:1)

Ala Gly Xaa1 Xaa2 Xaa3 Ser Arg Ala Arg Xaa4 Xaa5 Xaa6 Ala Arg Gly Cys
Arg Leu Arg Ser Gln Leu Val Pro Val Xaa7 Ala Leu Gly Leu Gly His Xaa8 Ser
Asp Glu Leu Xaa9 Arg Phe Arg Phe Cys Ser Gly Ser Cys Arg Arg Ala Arg
Ser Xaa10 His Asp Leu Ser Leu Ala Ser Leu Leu Gly Ala Gly Ala Leu Arg
Xaa11 Pro Pro Gly Ser Arg Pro Xaa12 Ser Gln Pro Cys Cys Arg Pro Thr Arg
Tyr Glu Ala Val Ser Phe Met Asp Val Asn Ser Thr Trp Arg Thr Val Asp
Xaa13 Leu Ser Ala Thr Ala Cys Gly Cys Leu Gly wherein:

| | | |
|---|---|---|
| $Xaa_1$ is Gly or Thr | $Xaa_6$ is Gly or Asp | $Xaa_{11}$ is Pro or Ser |
| $Xaa_2$ is Pro or Arg | $Xaa_7$ is Arg or Ser | $Xaa_{12}$ is Val or Ile |
| $Xaa_3$ is Gly or Ser | $Xaa_8$ is Arg or Ser | $Xaa_{13}$ is Arg or His |
| $Xaa_4$ is Ala or Thr | $Xaa_9$ is Val or Ile | |
| $Xaa_5$ is Ala or Thr | $Xaa_{10}$ is Pro or Gln | |

FIG. 5

```
          ....|....|....|....|....|....|....|....|....|....|....|....|
PrePro    ------------------MLGLGGLSTLSHCPWPRRQPALWPTLAALALL  33
NBN140    --------------------------------------------------
NBN116    --------------------------------------------------
NBN113    --------------------------------------------------

....|....|....|....|....|....|....|....|....|....|....|....|
PrePro    SSVAEASLGSAPRSPAPREGPPPVLASPAGHLPGGRTARWCSGRARRPPP  83
NBN140    ----------------------------------------------PPP   3
NBN116    --------------------------------------------------
NBN113    --------------------------------------------------

....|....|....|....|....|....|....|....|....|....|....|....|
PrePro    QPSRPAPPPPAPPSALPRGGRAARAGGPGSRARAAGARGCRLRSQLVPVR 133
NBN140    QPSRPAPPPPAPPSALPRGGRAARAGGPGSRARAAGARGCRLRSQLVPVR  53
NBN116    ---------------------AARAGGPGSRARAAGARGCRLRSQLVPVR  29
NBN113    ------------------------AGGPGSRARAAGARGCRLRSQLVPVR  26
                                                          *

....|....|....|....|....|....|....|....|....|....|....|....|
PrePro    ALGLGHRSDELVRFRFCSGSCRRARSPHDLSLASLLGAGALRPPPGSRPV 183
NBN140    ALGLGHRSDELVRFRFCSGSCRRARSPHDLSLASLLGAGALRPPPGSRPV 103
NBN116    ALGLGHRSDELVRFRFCSGSCRRARSPHDLSLASLLGAGALRPPPGSRPV  79
NBN113    ALGLGHRSDELVRFRFCSGSCRRARSPHDLSLASLLGAGALRPPPGSRPV  76
                         #   +

....|....|....|....|....|....|....|....|....|....|..
PrePro    SQPCCRPTRYEAVSFMDVNSTWRTVDRLSATACGCLG 220   (SEQ ID NO:5)
NBN140    SQPCCRPTRYEAVSFMDVNSTWRTVDRLSATACGCLG 140   (SEQ ID NO:6)
NBN116    SQPCCRPTRYEAVSFMDVNSTWRTVDRLSATACGCLG 116   (SEQ ID NO:7)
NBN113    SQPCCRPTRYEAVSFMDVNSTWRTVDRLSATACGCLG 113   (SEQ ID NO:2)
           *                              # +
```

FIG. 6

```
                    10         20         30         40         50
             ....|....|....|....|....|....|....|....|....|....|
NBN113       AGGPGSRARAAGARGCRLRSQLVPVRALGLGHRSDELVRFRFCSGSCRRA  50
NBN112       -GGPGSRARAAGARGCRLRSQLVPVRALGLGHRSDELVRFRFCSGSCRRA  49
NBN111       --GPGSRARAAGARGCRLRSQLVPVRALGLGHRSDELVRFRFCSGSCRRA  48
NBN110       ---PGSRARAAGARGCRLRSQLVPVRALGLGHRSDELVRFRFCSGSCRRA  47
NBN109       ----GSRARAAGARGCRLRSQLVPVRALGLGHRSDELVRFRFCSGSCRRA  46
NBN108       -----SRARAAGARGCRLRSQLVPVRALGLGHRSDELVRFRFCSGSCRRA  45
NBN107       ------RARAAGARGCRLRSQLVPVRALGLGHRSDELVRFRFCSGSCRRA  44
NBN106       -------ARAAGARGCRLRSQLVPVRALGLGHRSDELVRFRFCSGSCRRA  43
NBN105       --------RAAGARGCRLRSQLVPVRALGLGHRSDELVRFRFCSGSCRRA  42
NBN104       ---------AAGARGCRLRSQLVPVRALGLGHRSDELVRFRFCSGSCRRA  41
NBN103       ----------AGARGCRLRSQLVPVRALGLGHRSDELVRFRFCSGSCRRA  40
NBN102       -----------GARGCRLRSQLVPVRALGLGHRSDELVRFRFCSGSCRRA  39
NBN101       ------------ARGCRLRSQLVPVRALGLGHRSDELVRFRFCSGSCRRA  38
NBN100       -------------RGCRLRSQLVPVRALGLGHRSDELVRFRFCSGSCRRA  37
NBN99        --------------GCRLRSQLVPVRALGLGHRSDELVRFRFCSGSCRRA  36
                            *                              #  +

60         70         80         90        100
             ....|....|....|....|....|....|....|....|....|....|
NBN113       RSPHDLSLASLLGAGALRPPPGSRPVSQPCCRPTRYEAVSFMDVNSTWRT  100
NBN112       RSPHDLSLASLLGAGALRPPPGSRPVSQPCCRPTRYEAVSFMDVNSTWRT  99
NBN111       RSPHDLSLASLLGAGALRPPPGSRPVSQPCCRPTRYEAVSFMDVNSTWRT  98
NBN110       RSPHDLSLASLLGAGALRPPPGSRPVSQPCCRPTRYEAVSFMDVNSTWRT  97
NBN109       RSPHDLSLASLLGAGALRPPPGSRPVSQPCCRPTRYEAVSFMDVNSTWRT  96
NBN108       RSPHDLSLASLLGAGALRPPPGSRPVSQPCCRPTRYEAVSFMDVNSTWRT  95
NBN107       RSPHDLSLASLLGAGALRPPPGSRPVSQPCCRPTRYEAVSFMDVNSTWRT  94
NBN106       RSPHDLSLASLLGAGALRPPPGSRPVSQPCCRPTRYEAVSFMDVNSTWRT  93
NBN105       RSPHDLSLASLLGAGALRPPPGSRPVSQPCCRPTRYEAVSFMDVNSTWRT  92
NBN104       RSPHDLSLASLLGAGALRPPPGSRPVSQPCCRPTRYEAVSFMDVNSTWRT  91
NBN103       RSPHDLSLASLLGAGALRPPPGSRPVSQPCCRPTRYEAVSFMDVNSTWRT  90
NBN102       RSPHDLSLASLLGAGALRPPPGSRPVSQPCCRPTRYEAVSFMDVNSTWRT  89
NBN101       RSPHDLSLASLLGAGALRPPPGSRPVSQPCCRPTRYEAVSFMDVNSTWRT  88
NBN100       RSPHDLSLASLLGAGALRPPPGSRPVSQPCCRPTRYEAVSFMDVNSTWRT  87
NBN99        RSPHDLSLASLLGAGALRPPPGSRPVSQPCCRPTRYEAVSFMDVNSTWRT  86
                           *

110
             ....|....|...
NBN113       VDRLSATACGCLG  113    (SEQ ID NO:2)
NBN112       VDRLSATACGCLG  112    (SEQ ID NO:8)
NBN111       VDRLSATACGCLG  111    (SEQ ID NO:9)
NBN110       VDRLSATACGCLG  110    (SEQ ID NO:10)
NBN109       VDRLSATACGCLG  109    (SEQ ID NO:11)
NBN108       VDRLSATACGCLG  108    (SEQ ID NO:12)
NBN107       VDRLSATACGCLG  107    (SEQ ID NO:13)
NBN106       VDRLSATACGCLG  106    (SEQ ID NO:14)
NBN105       VDRLSATACGCLG  105    (SEQ ID NO:15)
NBN104       VDRLSATACGCLG  104    (SEQ ID NO:16)
NBN103       VDRLSATACGCLG  103    (SEQ ID NO:17)
NBN102       VDRLSATACGCLG  102    (SEQ ID NO:18)
NBN101       VDRLSATACGCLG  101    (SEQ ID NO:19)
NBN100       VDRLSATACGCLG  100    (SEQ ID NO:20)
NBN99        VDRLSATACGCLG   99    (SEQ ID NO:21)
                      # +
```

POLYMER CONJUGATED GLYCOSYLATED NEUBLASTIN

CROSS REFERENCE TO RELATED APPLICATIONS

This application is a national phase filing under 35 U.S.C. §371 of international application number PCT/US2004/011745, filed Apr. 16, 2004, which claims the benefit of priority of U.S. provisional application No. 60/463,899, filed Apr. 18, 2003. The disclosures of the prior applications are considered part of (and are incorporated by reference in) the disclosure of this application.

FIELD OF THE INVENTION

The invention relates to protein chemistry, molecular biology, neurobiology, neurology, and pain management.

BACKGROUND OF THE INVENTION

Neurotrophic factors are naturally-occurring proteins that regulate neuronal survival during development and regulate plasticity and structural integrity of the adult nervous system. These neurotrophic factors can be classified into superfamilies, families, subfamilies and individual species based on their structure and function.

Neurotrophic factor superfamilies include the fibroblast growth factor (FGF) superfamily, the neurotrophin superfamily, and the transforming growth factor-β (TGF-β) superfamily. The glial cell line-derived neurotrophic factor (GDNF)-related ligands are a family of proteins within the TGF-β superfamily. GDNF-related ligands include GDNF, persephin (PSP), neurturin (NTN) and neublastin (NBN; known as artemin or enovin). Members of the GDNF-related ligand family are distinguished by, among other things, their seven conserved cysteine residues. These residues form intramolecular and intermolecular disulfide bridges and give rise to the tertiary and quaternary structure of the dimerized polypeptide ligand. Members of the family also induce signaling through a multicomponent receptor complex consisting of a glycosylphosphatidylinositol (GPI)-anchored co-receptor of the GFRα family, a member of the GDNF-related ligand subfamily, and the RET tyrosine kinase receptor.

Activated RET initiates a signal transduction cascade that is responsible, at least in part, for the downstream effects of GDNF-related ligands.

Neublastin is classified within the GDNF family because it shares regions of homology with other GDNF ligands including the seven cysteine motif (e.g., as described in EP02/02691, PCT publications US02/02319 and US02/06388), and because binds to, and activates, the RET receptor as part of a GFRα complex. Neublastin is highly selective for binding to the GFRα3-RET receptor complex. In that respect, neublastin contains unique sub regions in its amino acid sequence as compared with other members of the GDNF-related ligand family.

Administration of neublastin is potentially useful in the treatment of diseases associated with neuronal degeneration and dysfunction. However, neublastin is rapidly cleared by the body, which may affect the neublastin dosing paradigm required in therapeutic applications. There is a need for molecules that display the biological activity of neublastin while exhibiting enhanced potency.

SUMMARY OF THE INVENTION

It has been discovered that when a neublastin protein, i.e., a dimer, is internally glycosylated and amino terminal-conjugated to a water-soluble synthetic polymer, e.g., polyethylene glycol (PEG), bioavailability and serum half-life are significantly enhanced. Therefore, in vivo efficacy is achieved at lower doses.

Based on this discovery, the invention features a dimer containing a first neublastin polypeptide and a second neublastin polypeptide, wherein: (a) at least one of the polypeptides is glycosylated; (b) at least one of the polypeptides is conjugated at its N-terminus to a water-soluble synthetic polymer; and (c) neither of the polypeptides is conjugated to a water-soluble synthetic polymer at a position other than the N-terminus.

The neublastin polypeptide(s) can be, e.g., NBN113 (SEQ ID NO:2), NBN140 (SEQ ID NO:6), NBN116 (SEQ ID NO:7), NBN112 (SEQ ID NO:8), NBN111 (SEQ ID NO:9), NBN110 (SEQ ID NO:10), NBN109 (SEQ ID NO:11), NBN208 (SEQ ID NO:12), NBN107 (SEQ ID NO:13), NBN106 (SEQ ID NO:14), NBN105 (SEQ ID NO:15), NBN104 (SEQ ID NO:16), NBN103 (SEQ ID NO:17), NBN102 (SEQ ID NO:18), NBN101 (SEQ ID NO:19), NBN100 (SEQ ID NO:20) and NBN99 (SEQ ID NO:21). A preferred polypeptide for incorporation into the dimer is NBN104 (SEQ ID NO: 16).

In some embodiments, the amino acid sequence of the first neublastin polypeptide and the second neublastin polypeptide are the same. Preferably, the water-soluble synthetic polymer is a polyalkylene glycol, e.g., polyethylene glycol (PEG).

Preferably, the average total molecular weight of the polyalkylene glycol moiety or moieties conjugated to the dimer is 10-50 kDa; more preferably 1545 kDa; and most preferably 2040 kDa. The polyalkylene glycol moiety can be linear or branched.

The invention provides a composition comprising the dimer of claim 1 and a pharmaceutically acceptable carrier.

The invention provides a method of treating neuropathic pain in a mammal, e.g., a human patient. The method includes administering to the mammal a therapeutically effective amount of a dimer of the invention. The invention provides a method of treating tactile allodynia in a mammal. The method includes administering to the mammal a therapeutically effective amount of a dimer of the invention. The invention provides a method of treating thermal hyperalgesia in a mammal. The method includes administering to the mammal a therapeutically effective amount of a dimer of the invention. The invention provides a method of activating the RET receptor in a mammal. The method includes administering to the mammal an effective amount of a dimer of the invention.

In some embodiments of the invention, the therapeutically effective amount is from 0.1 μg/kg to 1000 μg/kg. In some embodiments, the therapeutically effective amount is from 1 μg/kg to 100 μg/kg. In some embodiments, the therapeutically effective amount is from 1μg/kg to 30 μg/kg. In some embodiments, the therapeutically effective amount is from 3 μg/kg to 10 μg/kg. Preferably, the route of administration is intramuscular or subcutaneous.

Unless otherwise defined, all technical and scientific terms used herein have the same meaning as commonly understood by one of ordinary skill in the art to which this invention belongs. Although methods and materials similar or equivalent to those described herein can be used in the practice of the invention, suitable methods and materials are described below. All publications, patent applications, patents, and other references mentioned herein are incorporated by reference in their entirety. In the case of conflict, the present specification, including definitions, will control.

Unless otherwise stated, any reference to a neublastin polypeptide amino acid residue number corresponds to the numbering in SEQ ID NO:1.

As used herein, "consensus neublastin" means the sequence of SEQ ID NO:1

As used herein, "neublastin polypeptide" means a polypeptide that (1) displays at least one biological activity of neublastin when dimerized as a homodimer, and (2) includes an amino acid sequence at least 90% identical to amino acids 8-113 of SEQ ID NO:2.

As used herein, "wild-type neublastin polypeptide" means a polypeptide whose amino acid sequence is a naturally-occurring neublastin polypeptide sequence. Examples of wild-type neublastins are human neublastin (SEQ ID NO:2), mouse neublastin (SEQ ID NO:3), and rat neublastin (SEQ ID NO:4).

Percent identity between amino acid sequences can be determined using the BLAST 2.0 program (available at www.ncbi.nlm.nih.gov/BLAST) or a subsequent version thereof. Sequence comparison can be performed using an ungapped alignment and using the default parameters (Blossom 62 matrix, gap existence cost of 11, per residue gap cost of 1, and a lambda ratio of 0.85). The mathematical algorithm used in BLAST programs is described in Altschul et al., 1997, *Nucleic Acids Research* 25:3389-3402.

Other features and advantages of the invention will be apparent from the following detailed description and claims.

BRIEF DESCRIPTION OF THE DRAWINGS

FIG. 3 is an alignment of mature, wild-type neublasfin sequences from human, mouse, and rat. Also shown is a consensus sequence based on the human, mouse and rat sequences.

FIG. 4 is a consensus sequence based on human, mouse and rat neublastin sequences, with optional amino acid substitutions indicated.

FIG. 5 is an alignment of the wild-type human neublastin prepro sequence, and three different mature, human neublastin sequences produced naturally by alternative post-translational processing.

FIG. 6 is an amino acid sequence alignment of various truncations of the 113-amino acid form of wild-type human neublastin that can be incorporated into dimers of the invention.

DETAILED DESCRIPTION OF THE INVENTION

Polymer-Conjugated, Glycosylated Neublastin Dimers

Figure 1:
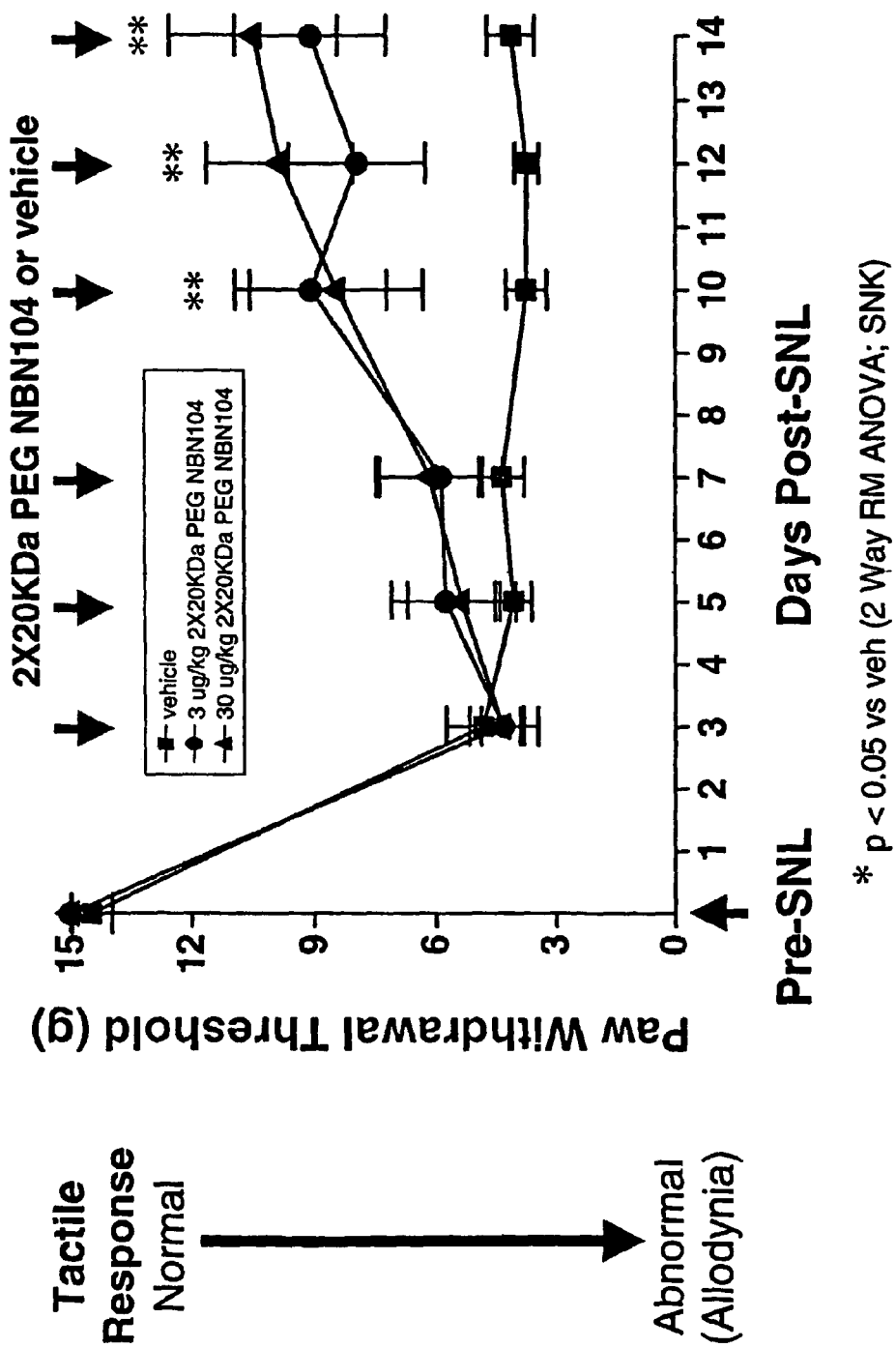
FIG. 1 is a broken line plot summarizing data showing substantial reversal of fully established tactile allodynia by subcutaneous administration of a homodimer of NBN104 wherein each monomer is conjugated to a PEG moiety at its amino terminus, and glycosylated at position 95 ("2×20 kDa PEG NBN104"), in rats with L5/L6 spinal nerve ligation.

Dimers of the invention display activity in assays for biological activity of neublastin. For example, dimers of the invention are active in RET activation assays. Dimers of the invention display enhanced bioavailability and/or longer serum half-life relative to the corresponding dimer without the combination of polymer conjugation and glycosylation. In preferred embodiments of the invention, the polymer-conjugated, glycosylated dimer displays significantly increased potency in vivo, relative to the potency of the corresponding polypeptide without polymer conjugation and glycosylation.

In general, polypeptides incorporated into dimers of the invention retain at least one of the following features:
(i) seven conserved cysteine residues at positions corresponding to residues 16, 43, 47, 80, 81, 109, and 111 in SEQ ID NO:1;
(ii) amino acid residues as follows:
C at position 16, L at position 18, V at position 25, L at position 28, G at position 29, L at position 30, G at position 31, E at position 36, F at position 40, R at position 41, F at position 42, C at position 43, G at position 45, C at position 47, C at position 80, C at position 81, R at position 82, P at position 83, F at position 91, D at position 93, N at position 95, S at position 105, A at position 106, C at position 109 and C at position 111;
(iii) an LGLG repeat, an FRFC motif, a QPCCRP motif, and a SATACGC motif Preferably, the polypeptides retain all of the above features.

Examples of wild-type neublastin polypeptide amino acid sequences are presented in FIG. 3. Regarding wild-type neublastin polypeptides and sequences, see PCT publication WO 00/01815. A neublastin consensus sequence (consensus with respect to human, mouse and rat) is presented in FIG. 4.

The sequence of the human prepro neublastin (SEQ ID NO:5) is shown in FIG. 5. Three mature forms of human neublastin resulting from different post-translational processing have been identified. The three forms are:
(i) the 140 AA polypeptide designated NBN140 (SEQ ID NO:6);
(ii) the 116 AA polypeptide designated NBN116 (SEQ ID NO:7); and
(iii) the 113 AA polypeptide designated NBN113 (SEQ ID NO:2).

FIG. 5 is an alignment comparing the human prepro neublastin amino acid sequence and the three mature sequences. Line 1 provides the polypeptide of SEQ ID NO:5, line 2 provides the polypeptide of SEQ ID NO:6, line 3 provides the polypeptide of SEQ ID NO:7 and line 4 provides the polypeptide of SEQ ID NO:2. The seven conserved cysteine residues are designated by symbols ("*", "#", "+" and "|") to indicate the intramolecular (* with *, # with #, and +with +) and intermolecular ("|") disulfide bridges formed in the mature dimerized neublastin ligand.

Neublastin polypeptides in dimers of the invention may be products of a protease cleavage reaction or a chemical cleavage reaction, or may be expressed directly from recombinant DNA construct. Alternatively, they can be chemically synthesized, e.g., using a commercial, solid phase synthesizer.

A preferred polymer-conjugated neublastin polypeptide dimer is a homodimer of NBN104 wherein each monomer is conjugated to a PEG moiety at its amino terminus, and glycosylated at position 95 ("2×20 kDa PEG NBN104"). In some embodiments, the polypeptide in the dimer consists essentially of amino acids 8-113 of SEQ ID NO:1.

In preferred embodiments of the invention, the dimer binds to GFRα3 and stimulates tyrosine phosphorylation of a RET polypeptide. In some embodiments, the dimer enhances survival of a sensory neuron, or reduces or reverses pathological changes of a sensory neuron. In some embodiments, the dimer enhances survival of an autonomic neuron or a dopaminergic neuron.

The invention provides a method for making a polymer conjugated glycosylated neublastin polypeptide dimer. The method includes providing a glycosylated neublastin dimer, e.g., from a eukaryotic cell, and conjugating at least one polypeptide in the dimer to a water-soluble, synthetic polymer, e.g., a polyalkylene glycol moiety.

Neublastin Polypeptides

Neublastin polypeptides can be produced by recombinant DNA techniques. For example, a nucleic acid sequence encoding a neublastin polypeptide can be inserted into a vector, e.g., an expression vector, and the vector can be introduced into a suitable host cell. Suitable host cells are those that glycosylate polypeptides. Eukaryotic host cells are preferred. However, at least one bacterium, i.e., *Campylobacter jejuni*, contains an N-linked glycosylation system that can be transferred into bacterial host cells such as *E. coli* (Wacker et al., 2002, Science 298:1790-1793). Chemical modification and/or extension of a bacterial glycosylation can be achieved in vitro, using methods and materials known in the art. Thus, a glycosylation-competent bacterial system optionally can be used to produce neublastin polypeptides for use according to the invention.

Neublastin polypeptides suitable for use in the invention can be produced in a mammalian cell, e.g., a human embryonic kidney ("HEK") cell such as a HEK 293 cell, a BHK21 cell, or a Chinese hamster ovary ("CHO") cell. Other suitable mammalian cells include PC12, HiB5, RN33b cell lines, human neural progenitor cells, and other cells derived from human cells, especially neural cells. Examples of immortalized human cell lines useful in practicing the invention include Bowes Melanoma cells (ATCC Accession No. CRL 9607), Daudi cells (ATCC Accession No. CCL 213), HeLa cells and derivatives of HeLa cells (ATCC Accession Nos. CCL 2, CCL 2.1, and CCL 2.2), HL-60 cells (ATCC Accession No. CCL 240), HT-1080 cells (ATCC Accession No. CCL 121), Jurkat cells (ATCC Accession No. TIB 152), KB carcinoma cells (ATCC Accession No. CCL 17), K-562 leukemia cells (ATCC Accession No. CCL 243), MCF-7 breast cancer cells (ATCC Accession No. BTH 22), MOLT-4 cells (ATCC Accession No. 1582), Namalwa cells (ATCC Accession No. CRL 1432), Raji cells (ATCC Accession No. CCL 86), RPMI 8226 cells (ATCC Accession No. CCL 155), U-937 cells (ATCC Accession No. CRL 1593), WI-38VA13 sub line 2R4 cells (ATCC Accession No. CLL 75.1), and 2780AD ovarian carcinoma cells (Van der Blick et al., *Cancer Res.* 48: 5927-5932, 1988). Secondary human fibroblast strains, such as WI-38 (ATCC Accession No. CCL 75) and MRC-5 (ATCC Accession No. CCL 171), also can be used.

Suitable non-mammalian host cells include *Xenopus laevis* oocyte ("XLO") and yeast cells such as *Pichia pastoris*. In some embodiments, the host cell is an insect cell such as an Sf9 cell.

Transformation of the host cell can be by any suitable method, including, e.g., infection (employing a virus vector), by transfection (employing a plasmid vector), using calcium phosphate precipitation, microinjection, electroporation, and lipofection. Methods and materials for eukaryotic host cell transformation are known in the art.

Neublastin polypeptides produced by transformed host cells can be isolated from the cells or from the host cell culture medium, using conventional protein purification techniques. Refolding steps can be employed as necessary.

Neublastin polypeptides can be modified using conventional methods and materials. One such method is site-directed mutagenesis, in which one or more nucleotides are changed in order to effect a predetermined substitution of one or more amino acids in a neublastin polypeptide. Suitable site-directed mutagenesis kits are commercially available, e.g., "Transformer Site Directed Mutagenesis Kit" (Clontech Laboratories, Palo Alto, Calif.).

Some embodiments of the invention involve neublastin polypeptides containing conservative amino acid substitutions. Conservative amino acid substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

The glycosylated neublastin may be provided in any bioactive form, including the form of pre-pro-proteins, pro-proteins, mature proteins, phosphorylated proteins, non-phosphorylated proteins, truncated forms, or any other posttranslational modified protein. In some embodiments, a polypeptide of the invention has the amino acid sequence presented as SEQ ID NO:6, holding a glycosylated asparagine residue at position 122; or the amino acid sequence presented as SEQ ID NO:14, holding a glycosylated asparagine residue at position 95, or the analogous position in any neublastin polypeptide when aligned by, e.g., ClustalW computer software.

In general, a dimer isolated from a mammalian cell, or other such cell able to glycosylate proteins, will be glycosylated at amino acid position 95. Methods of glycosylating proteins in vitro are known in the art and may be employed to glycosylate neublastin polypeptides or polypeptide dimers if so desired.

Practice of the present invention can be carried out using conventional techniques of cell biology, cell culture, molecular biology, microbiology, recombinant DNA, protein chemistry, and immunology. Such techniques are described in general references. See, e.g., *Molecular Cloning: A Laboratory Manual,* 2nd Ed. (Sambrook et al., eds.), Cold Spring Harbor Laboratory Press, 1989; *DNA Cloning,* Vol. I and II (Glover, ed), 1985; *Oligonucleotide Synthesis,* (Gait, ed.), 1984; Mullis et al. U.S. Pat. No. 4,683,195; *Nucleic Acid Hybridization* (Haines et al., eds.), 1984; *Transcription and Translation* (Hames et al., eds.), 1984; *Culture of Animal Cells* (Freshney, ed) Alan R. Liss, Inc., 1987; *Immobilized Cells and Enzymes,* IRL Press, 1986; *A Practical Guide to Molecular Cloning,* 1984; *Meth. Enzymol.,* Vol. 154 and 155 (Wu et al., eds), Academic Press, New York; *Gene Transfer Vectors for Mammalian Cells* (Miller et al., eds.), 1987, Cold Spring Harbor Laboratory; *Immunochernical Methods in Cell and Molecular Biology* (Mayer et al., eds.), Academic Press, London, 1987.

Polymer Conjugation of Neublastin Polypeptides

The polymer conjugated to a neublastin polypeptide is water-soluble. Preferably, the polymer is suitable for use in a pharmaceutical composition. Examples of suitable water-soluble polymers include PEG, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) PEG, propropylene glycol homopolymers, polypropylene oxide/ethylene oxide co-polymers, polyoxyethylated polyols (e.g., glycerol), polyvinyl alcohol, and mixtures thereof.

Average molecular weight per polymer chain is chosen in accordance with the desired average total molecular weight of the polymer(s) conjugated per dimer, e.g., 10-50 kDa, 15-45 kDa, or 20-40 kDa per dimer. In PEG preparations, some molecules weigh more, some less, than the stated molecular weight. Thus, molecular weight is typically specified as "average molecular weight." Various conjugation methods are known in the art. See, e.g., EP 0 401384 (coupling PEG to G-CSF); Malik et al., Exp. Hematol. 20: 1028-1035, 1992 (PEGylation of GM-CSF using tresyl chloride).

PEGylation can be carried out by any suitable PEGylation reaction. Various PEGylation chemistries are known in the art. See, e.g., Focus on Growth Factors, 3 (2): 4-10, 1992; EP 0 154 316; EP 0 401 384; and the other publications cited herein that relate to PEGylation. The PEGylation may be carried out via an acylation reaction or an alkylation reaction with a reactive PEG molecule (or other suitable reactive water-soluble polymer).

PEGylation by acylation generally involves reacting an active ester derivative of PEG. Any known or subsequently discovered reactive PEG molecule may be used to carry out the PEGylation. A preferred activated PEG ester is PEG esterified to N-hydroxysuccinimide (NHS). As used herein, "acylation" includes without limitation the following types of linkages between the therapeutic protein and a water soluble polymer such as PEG: amide, carbamate, urethane, and the like. See, *Bioconjugate Chem.* 5: 133-140, 1994. Reaction conditions may be selected from any of those known in the PEGylation art or those subsequently developed, but should avoid conditions such as temperature, solvent, and pH that would inactivate the neublastin protein or polypeptide to be modified.

In general, PEGylation by acylation results in a poly-PEGylated polypeptide. In the case of neublastin, however, there are no lysine residues. Therefore, PEGylation by acylation can be employed to obtain a polypeptide PEGylated exclusively at the amino terminus. PEGylated polypeptides can be separated from the reaction mixture and unreacted polypeptides, by conventional techniques, e.g., dialysis, salting-out, ultrafiltration, ion- exchange chromatography, gel filtration chromatography and electrophoresis.

PEGylation by alkylation generally involves reacting a terminal aldehyde derivative of PEG with neublastin polypeptide or dimer in the presence of a reducing agent. In general, PEGylation by alkylation can result in poly-PEGylated polypeptides, and one can manipulate the reaction conditions to favor PEGylation at at the amino terminus. However, since neublastin contains no lysine residues, such manipulation need not be done. The PEG groups are preferably attached to the protein via a —CH$_2$—NH— group, i.e., through an "alkyl" linkage.

The polymer molecules used in both the acylation and alkylation approaches may be selected from among water-soluble polymers as described above. The polymer selected should be modified to have a single reactive group, such as an active ester for acylation or an aldehyde for alkylation, preferably, so that the degree of polymerization may be controlled as provided for in the present methods. An exemplary reactive PEG aldehyde is PEG propionaldehyde, which is water stable, or mono C1-C10 alkoxy or aryloxy derivatives thereof (see, U.S. Pat. No. 5,252,714). The polymer may be branched or unbranched. For the acylation reactions, the polymer(s) selected should have a single reactive ester group. For the present reductive alkylation, the polymer(s) selected should have a single reactive aldehyde group. For purposes of the invention, the PEG can be any of the forms of PEG known in the art for derivatization of other proteins, including mono-(C1-C10) alkoxy- and aryloxy-PEG.

Formulations

Compositions containing dimers of the invention may contain suitable pharmaceutically acceptable carriers. For example, they may contain excipients and/or auxiliaries that facilitate processing of the dimers into preparations designed for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension, for example, sodium carboxymethyl cellulose, sorbitol and dextran. Optionally, the suspension may also contain stabilizers. Liposomes also can be used to encapsulate the molecules of the invention for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In some embodiments, the compositions include pharmaceutically acceptable substances such as wetting or emulsifying agents, preservatives or buffers.

Compositions of the invention may be in a variety of forms, including, for example, liquid (e.g., injectable and infusible solutions), dispersions, suspensions, semi-solid and solid dosage forms. The preferred form depends on the mode of administration and therapeutic application.

The composition can be formulated as a solution, micro emulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by a coating such as lecithin, by the maintenance of the required particle size in the case of dispersion, and by surfactants. Prolonged absorption of injectable compositions can be achieved by including in the composition an agent that delays absorption. Examples of such agents are monostearate salts and gelatin.

The active ingredient can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See e.g., Sustained and Controlled Release Drug Delivery Systems, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the formulation. For example, a dimer according to the invention can be coadministered with an analgesic.

Dosage regimens may be adjusted to provide the optimum desired response. For example, a single bolus may be administered, several divided doses may be administered over time, or the dose may be proportionally reduced or increased as indicated by the exigencies of the therapeutic situation. It is advantageous to formulate parenteral compositions in dosage unit form for ease of administration and uniformity of dosage. See generally, *Remington's Pharmaceutical Sciences* (Mack Pub. Co., Easton, Pa. 1980).

In addition to a dimer of the invention, a liquid dosage form may contain inert ingredients such as water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfiryl alcohol, polyethylene glycols, and fatty acid esters of sorbitan.

Methods of Treatment

The invention is useful for treatment of sensory neurons, retinal ganglion cells, neurons in the dorsal root ganglia, and neurons in any of the following tissues: the geniculate, petrosal and nodose ganglia; the vestibuloacoustic complex of the eighth cranial nerve; the ventrolateral pole of the maxillomandibular lobe of the trigeminal ganglion; and the mesencephalic trigeminal nucleus.

Compositions and methods of the invention can be used to treat sensory neurons, autonomic neurons, or both. Nociceptive and mechanoreceptive neurons can be treated, e.g., A-delta fiber, C-fiber and A-beta fiber neurons. In addition, sympathetic and parasympathetic neurons of the autonomic system can be treated.

Neuropathic Pain

When used in treatment of neuropathic pain, a dimer of the invention can be administered alone or in conjunction with an analgesic agent. Examples of an analgesic agent include an opioid, an anti-arrhythmic, a topical analgesic, a local anaesthetic, an anticonvulsant, an antidepressant, a corticosteroid or non-steroidal anti-inflammatory drug (NSAID). Preferred analgesic agents are gabapentin ((1-aminomethyl)cyclohexane acetic acid); and pregabalin (S-(+)-4-amino-3-(2-methylpropyl) butanoic acid).

Dimers of the invention can be used in the treatment of pain associated with peripheral neuropathies. Peripheral neuropathies that can be treated according to this invention include trauma-induced neuropathies, physical damage to the brain, physical damage to the spinal cord, and stroke.

The invention also provides treatments of chemotherapy-induced neuropathies, other drug induced neuropathies, pathogen-induced neuropathies, toxin-induced neuropathies, vitamin-deficiency-induced neuropathies; idiopathic neuropathies; and diabetic neuropathies. The invention also can be used to treat mono-neuropathies, mono-multiplex neuropathies, and poly-neuropathies, including axonal and demyelinating neuropathies.

Examples of chemotherapy-induced neuropathies include neuropathies caused by exposure to chemotherapeutic agents such as taxol, taxotere, cisplatin, nocodazole, vincristine, vindesine or vinblastine. Examples of other drug induced neuropathies incluce neuropathies caused by ddI, DDC, d4T, foscarnet, dapsone, metronidazole, and isoniazid. Examples of toxin-induced neuropathies include neuropathies induced by alcoholism, vitamin B6 intoxication, hexacarbon intoxication, amiodarone, chloramphenicol, disulfiram, isoniazide, gold, lithium, metronidazole, misonidazole, and nitrofurantoin. Examples of virus-induced neuropathies include neuropathies caused by a herpes zoster (which may lead to post-herpetic neuralgia), human immunodeficiency virus (HIV), and papilloma virus (HPV). Examples of vitamin-deficiency-induced neuropathies are those caused by vitamin B12 deficiency, vitamin B6 deficiency, and vitamin E deficiency. Other types of neuropathy that can be treated according to the invention include inflammation-induced nerve damage, neurodegeneration, hereditary neuropathy, e.g., Friedreich ataxia, familial amyloid polyneuropathy, Tangier disease, and Fabry disease, metabolic disorders, e.g., renal insufficiency and hypothyroidism, infectious and viral neuropathies, e.g., neuropathic pain associated with leprosy, and Lyme disease. Auto-immune neuropathies include Guillain-Barre syndrome, chronic inflammatory de-myelinating polyneuropathy, monoclonal gammopathy of undetermined significance and polyneuropathy, trigeminal neuralgia and entrapment syndromes, e.g., Carpel tunnel syndrome, and other neuropathic pain syndromes including post-traumatic neuralgia, phantom limb pain, multiple sclerosis pain, complex regional pain syndromes, e.g., reflex sympathetic dystrophy, causalgia, neoplasia-associated pain, vasculitic/angiopathic neuropathy, and sciatica.

Tactile Allodynia

Tactile allodynia is a condition in which pain is evoked by stimulation of the skin (e.g. touch) that is normally innocuous. Tactile allodynia can be treated by administering to the subject a pharmaceutically effective amount of a dimer of the invention. The dimer can be administered alone or in conjunction with an effective amount of an analgesic agent.

A dimer of the invention can be co-administered with a therapeutic agent such as an anti-cancer agent or an anti-viral agent. Examples of anti-cancer agents include taxol, taxotere, cisplatin, nocodazole, vincristine, vindesine and vinblastine.

Examples of anti-viral agents include ddI, DDC, d4T, foscarnet, dapsone, metronidazole, and isoniazid.

Reduction of Loss of Pain Sensitivity

Compositions of the invention can be used for reducing the loss of pain sensitivity, e.g., loss of thermal pain sensitivity, in a patient with diabetic neuropathy. Treatment can be prophylactic or therapeutic.

In prophylactic treatment, a dimer of the invention is administered to a patient at risk of developing loss of pain sensitivity, e.g., a patient with an early stage neuropathy.

In therapeutic treatment, a dimer of the invention is administered to a patient who has experienced loss of pain sensitivity as a result of a neuropathy, e.g., a late stage neuropathy.

Viral-Associated Neuropathies

Compositions and methods of the invention can be used for prophylactic treatment of neuropathies associated with viral or bacterial infection. Prophylactic treatment is indicated after determination of infection and before onset of neuropathic pain. During treatment, a dimer of the invention is administered to prevent appearance of neuropathic pain such as neuropathic pain associated with leprosy, Lyme disease, or neuropathic pain caused by a virus. Viruses that can cause neuropathic pain include herpes zoster virus (which may lead to post-herpetic neuralgia); human immunodeficiency virus (HIV); and human papilloma virus (HPV).

Symptoms of acute viral infection often include the appearance of a rash. Other symptoms include, for example, persistent pain in the affected area of the body. This is a common complication of a herpes zoster infection (shingles). Post-herpetic neuralgia can last for a month or more, and may appear several months after any rash-like symptoms have disappeared.

The invention also provides for therapeutic treatment of neuropathic pain associated with viral or bacterial infection. In therapeutic treatment, a dimer of the invention is administered to a patient who is experiencing neuropathic pain associated with infection.

Painful Diabetic Neuropathy

Compositions and methods of the invention can be used for prophylactic treatment of painful diabetic neuropathy. Prophylactic treatment of diabetic neuropathies would commence after the initial diagnosis of diabetes or diabetes-associated symptoms and before onset of neuropathic pain. Prophylactic treatment of painful diabetic neuropathy also may commence upon determining that a subject is at risk for developing diabetes or diabetes-associated symptoms. A dimer of the invention is administered to prevent appearance of neuropathic pain and/or to to reduce the severity of neuropathic pain that has already appeared.

The invention also provides for therapeutic treatment of neuropathic pain associated with diabetes. In therapeutic treatment, a dimer of the invention is administered to a patient who is experiencing neuropathic pain associated with diabetes.

Dosage and Route of Administration

Preferably, a formulation comprising a dimer of the invention is administered at a dosage from 0.1 µg/kg to 1 000 µg/kg body weight of the subject, per dose. Preferably the dosage is from 1 µg/kg to 100 µg/kg body weight of the subject, per dose. More preferably the dosage is from 1 µg/kg to 30 µg/kg body weight of the subject, per dose, e.g., from 3 µg/kg to 10 µg/kg body weight of the subject, per dose.

Therapeutically effective amounts of the formulation of the invention may be administered to a subject in need thereof in a dosage regimen ascertainable by one of skill in the art, without undue experimentation.

Administration dimer of the invention can be systemic or local. It can be administered by any suitable delivery system, e.g., intravenous delivery, intramuscular delivery, intrapulmonary delivery, subcutaneous delivery, and intraperitoneal delivery, most preferably via intramuscular delivery, intravenous delivery, or subcutaneous delivery. The dimer also can be administered intrathecally.

The invention is further illustrated in the following non-limiting examples.

EXAMPLES

Example 1

Expression in Mammalian Cells

Mature human Neublastin (HNBN) is naturally expressed as a pre-pro-protein. This polypeptide contains a signal peptide sequence for direction of the protein into the secretory pathway, a prodomain that is cleaved and discarded upon maturation, and a mature protein. The mature protein of 113 amino acids contains a single glycosylation site and seven cysteine residues. The seven cysteine residues are involved in three intramolecular disulfide linkages plus a single intermolecular disulfide bond to form a disulfide linked, glycosylated homodimer.

Construction of plasmid pJC070.14 In order to express the human neublastin cDNA in Chinese hamster ovary (CHO) cells, a cDNA fragment encoding the prepro form of human neublastin was inserted into the mammalian expression vector pEAG347 to generate plasmid pJCO70.14. The plasmid pEAG347 contained tandem SV40 early and adenovirus major late promoters (derived from plasmid pAD2beta; Norton et al., 1985, *Mol. Cell. Biol.* 5:281), a unique Not-I cloning site, followed by SV40 late transcription termination and polyA signals (derived from plasmid pCMVbeta; MacGregor et al., 1989, *Nucl. Acids. Res.* 17:2365). In addition, pEAG347 contained a pUC 19-derived plasmid backbone and a pSV2dhfr-derived dhfr for MTX selection and amplification in transfected CHO cells.

Plasmid pJC070.14 was generated in two steps. First, a fragment encoding the prepro form of human neublastin was isolated from plasmid pUbilZ-NBN using the polymerase chain reaction with oligonucleotides KD2-824 5'AAG-GAAAAAA GCGGCCGCCA TGGAACTTGG ACTTG-GAGG3' (SEQ ID NO:22), KD2-825 5'TTTTTTCCTT GGCGGCCGCT CAGCCCAGGC AGCCGCAGG3' (SEQ ID NO:23) and PFU polymerase. The fragment was cloned into the Srf-1 site of pPCR-Script Amp SK(+) to generate the plasmid pJC069. In the second step, a partial Not-1 digest was performed on plasmid pJC069 to generate a 685 bp fragment (containing the neublastin gene) which was cloned into the Not-1 site of plasmid pEAG347 to generate plasmid pJC070.14. Transcription of the neublastin gene in plasmid pJC070.14 was controlled by the adenovirus major late promoter.

CHO cell lines expressing human Neublastin. First, 200 µg of pJC070.14 was linearized by digestion with Mlu-1. Then 200 ug of sonicated salmon sperm DNA was added. The DNA was extracted with phenol:chloroform:isoamyl alcohol (25:24:1) and ethanol-precipitated. The linearized DNA was resuspended in 20 mM Hepes pH7.05, 137 mM NaCl, 5 mM KCl, 0.7 mM $Na_2HPO_4$, 6 mM dextrose (HEBS) and introduced into ~4E7 CHO dukx B1 (dhfr-) cells (p23) by electroporation (280V and 960 µF). Following electroporation, the cells were returned to culture in α+Modified Eagle's Medium (MEM) supplemented with 10% fetal bovine serum (FBS) for two days. The cells were then trypsinized and replated in 100 mm dishes (100,000 cells/plate) in α-MEM (lacking ribo- and deoxyribonucleosides), supplemented with 10% dialyzed FBS, for five days. The cells were subsequently split at a density of 100,000 cells/100 mm plate, and selected in 200 nM methotrexate. Resistant colonies were picked and scaled up to 6 well plates; conditioned media from each clone was screened using a specific assay for neublastin described below.

Twelve clones expressing the highest level of neublastin were scaled up to T162 flasks and subsequently re-assayed. These CHO cell lines produced neublastin in the range of 25-50 ng/ml/day. The four best neublastin-expressing cell lines were amplified in 1200 nM methotrexate and adapted to suspension culture in spinner flasks. The resulting clones produced approximately 2 ug/ml in high density spinner culture.

Ternary complex assay for Neublastin. The presence of neublastin was assessed in the media of CHO cell line supernatants using a modified form of a ternary complex assay. The assay was essentially as described by Sanicola et al., 1997, *Proc. Natl Acad Sci USA* 94:6238.

Expression of NBN104 in CHO Cells. A 104-amino acid form of mature hNBN was expressed in Chinese Hamster Ovary (CHO) cells by the following procedure. A synthetic hNBN gene was created using codons most commonly utilized for translation of proteins in CHO cells. A unique restriction endonuclease cleavage site was introduced. The codons for the rat albumin (rAlb) signal peptide, i.e., MKWVTFLLLLFISGSAFSAAGARG (SEQ ID NO:24), and the sequence for the human growth hormone (hGH), i.e., MATGSRTSLLLAFGLLCLSWLQEGSAAAGARG (SEQ ID NO:25), were fused independently to hNBN to create fusion genes (the signal peptide is in regular font and the NBN sequence is in italics; the hGH signal peptide includes an intron). Each fusion gene was placed under transcriptional control of a constitutive promoter and transfected into CHO cells. Stable transformants were isolated.

The cell lines were analyzed for expression of secreted hNBN. Data from reducing SDS-PAGE/Western blot analysis demonstrated the presence of a protein band corresponding to hNBN secreted into the medium. Further analysis of the conditioned medium demonstrated the presence of a titratable component in both a direct, antibody-driven assay as well as an indirect, cell-based, functional assay.

The conclusion is that functional HNBN can be expressed in CHO cells in the absence of a prodomain and with heterologous signal peptide sequences.

Example 2

Expression of Rat Neublastin in CHO Cells

Construction of plasmid pCWEX017.1. A gene for rat neublastin was generated by ligating two fragments that together encode rat neublastin. Plasmid pJC102 consisted of a DNA fragment encoding the first 156 amino acids of rat prepro form of neublastin inserted into the TOPO cloning site of pCRII-TOPO r (Invitrogen). The fragment was amplified from Marathon-Ready t rat liver cDNA (Clontech) using the polymerase chain reaction with oligonucleotides AP2 5'ACTCACTATAGGGCTC GAGCGGC3'(SEQ IDNO:26) and KD3-171 5'GAACCGCTGCAGAAGCGGAAACGTATC3' (SEQ ID NO:27). A fragment containing the prepro domain and first 29 amino acids of the mature 113 amino acid form of neublastin was first amplified using the polymerase chain reaction from the plasmid pJC102 with the oligonucleotides KD3-214 5'AAGGAAAAAAGCGGCCGCCATG-GAACTGGGACTTGGAGA3'(SEQ ID NO:28) and KD3-247 5'AGTTCGTCGGAAGAGTGTCCCAGGC-CGAGAGCGC TCACCG3'(SEQ ID NO:29). A second fragment encoding amino acids 30-113 of the mature 113 amino acid form of neublastin was amplified from PCWEX015 with the oligonucleotides KD3-246 5'CGGT-GAGCGCTCTCGGCCTGGGACACTCTT CCGAC-GAACT3'(SEQ ID NO:30) and KD3-219 5'TTTTTCCTTG-GCGGCCGCT CATCCTAGACAGCCACATG3'(SEQ ID NO:31). The plasmidpCWEX015 was generated by inserting a BamH1-Xho1 fragment from a syngene into the complementary sites of the expression plasmid pMJB134. The resultant DNA fragments were mixed at a 1:1 ratio and submitted to a second polymerase chain reaction with oligonucleotides KD3-214 and KD3-219 generating the full length prepro form of rat neublastin. The resultant DNA fragment was cloned into the TOPO cloning site of the plasmid pCRII blunt-topo to generate pCWEX016. A Not-1 fragment containing the entire prepro neublastin was isolated and cloned into the Not-1 Site of pEAG347 to make pCWEX017.1.

Sequence of Rat Neublastin Synthetic Gene (SEQ ID NO: 32)
```
GCTCGAGCGGCCATATCGACGACGACGACAAGGCTGGAACTCGCAGCTCT
CGTGCTCGTGCAACCGATGCACGTGGCTGTCGTCTGCGTTCTCAACTAGT
GCCGGTGTCTGCACTCGGACTGGGACACTCTTCCGACGAACTAATTCGTT
TTCGTTTTTGTTCAGGATCTTGTCGTCGTGCACGTTCTCCGCATGATCTA
TCTCTAGCATCTCTACTAGGAGCCGGAGCACTAAGATCTCCGCCGGGATC
TAGACCTATTTCTCAACCTTGTTGTAGACCTACTAGATACGAAGCAGTAT
CTTTCATGGACGTAAACTCTACATGGAGAACCGTAGATCATCTATCTGCA
ACCGCATGTGGCTGTCTAGGATGATAATAGGGATCCG
```

CHO cell lines expressing rat Neublastin. 200 μg of plasmid CWEX017.1 was linearized by digestion with the restriction endonuclease Mlu-1. After digestion, 200 ug of sonicated salmon sperm DNA was added and the mixture was extracted with phenol: chloroform:isoamyl alcohol (25:24:1) and ethanol precipitated. The linearized DNA was resuspended in 20 mM Hepes pH7.05, 137 mM NaCl, 5 mM KCl, 0.7 mM Na$_2$HPO$_4$, 6 mM dextrose (HEBS) and introduced into ~4E7 CHO DG44 (dhfr-) cells (p8) by electroporation (280V and 960 μF). Following electroporation, the cells were returned to culture in α+Modified Eagle's Medium (MEM) supplemented with 10% fetal bovine serum (FBS) for two days. The cells were then trypsinized and replated in 100 mm dishes (100,000 cells/plate) in α-MEM (lacking ribo- and deoxyribonucleosides), supplemented with 10% dialyzed FBS. After six days in culture, the media was replaced and the cells were selected in 200 nM methotrexate. Resistant colonies were picked and scaled up to 6 well plates; conditioned media from each clone was screened using the ternary complex assay for neublastin referenced above. The five clones expressing the highest level of neublastin were scaled up to T162 flasks and subsequently re-assayed. These CHO cell lines produced Neublastin in the range of 500 ng/ml/day. The highest expressing lines were subsequently adapted to suspension culture and express neublastin at approximately 2 ug/ml in high density spinner culture.

PEGylated CHO-derived rat neublastin. One hundred liters of CHO cells expressing rat NBN (clone 33s) were grown for 10 days at 37C in BCM16 medium containing 200 nM methotrexate. The culture was filtered and concentrated 10-fold. Hepes pH 7.5 was added to a final concentration of 10 mM and the medium was loaded overnight at 4C onto a 120 mL SP-Sepharose column (Pharmacia). The column was washed with 10 mM Hepes pH 7.5, 100 mM NaCl and bound protein eluted from the column with a gradient of NaCl (0.1-1M) in 10 mM Hepes pH 7.5. Samples were analyzed for absorbance at 280 nm, for total protein by SDS-PAGE, and for functional NBN using the RetL3 ternary complex ELISA. NBN activity was found at the trailing edge of the protein peak. Peak NBN-containing fractions from the SP column were pooled, diluted 5-fold with 10 mM Hepes 7.5, loaded onto a 22 mL Heparin Sepharose column (Pharmacia). The column was washed with 110 mL of 10 mM Hepes pH 7.5, 500 mM and NBN was eluted with 10 mM Hepes pH 7.5, 1M NaCl. NBN-containing fractions were identified by SDS-PAGE and pooled. The pooled fraction was diluted with 10 mM Hepes pH 7.5 to a final salt concentration of 150 mM. The protein was loaded onto a 20 mL SP-Sepharose column and again eluted with a gradient of NaCl. NBN-containing fractions were identified by SDS-PAGE, pooled, filtered and stored at −70C. Protein context was estimated from absorbance at 280 nm using an extinction coefficient of 0.5 for a 1 mg/mL solution. The purified CHO NBN migrated as a single broad band by SDS-PAGE under non-reducing conditions with an apparent mass of 36 kDa and under reducing conditions migrated as a band with an apparent mass of 18 kDa. N-terminal sequence analysis revealed that the N-terminus of the product was heterogenous due to cleavage at alternative sites producing des 1-4, des 1-7, and des 1-9 adducts.

To remove N-terminal heterogeneity in the purified NBN the protein was treated for 2 h at 37C at pH 8.5 with a 1:100 (w/w) ratio of trypsin to NBN and purified on a Superdex 75 gel filtration column in 10 mM Hepes pH 7.5, 300 mM NaCl. Peak NBN-containing fractions were identified by SDS-PAGE, pooled (0.9 mg/mL final), filtered through a 0.2 µm filter, aliquoted and stored at −70C for subsequent studies. N-terminal sequencing of the NBN after trypsin-treatment-revealed that the protein had been converted to a des 1-9, 104 amino acid form, starting with the sequence ATDARGC. Mass spectroscopy data for the reduced and deglycosylated product revealed a mass of 11104 Da, which agreed exactly with the predicted mass for the des 1-9 form of NBN.

The purified des 1-9 NBN was thawed at room temperature. Hepes pH 7.5 was added to 50 mM from a 1 M stock and 20K NHS-SPA PEG (Shearwarter Polymers, Inc.) was added to a final concentration of 8 mg PEG/mL. The final NBN concentration in the reaction was 0.7 mg/mL. The sample was incubated at room temperature for 3 h and then dialyzed overnight at 4C against 50 volumes of 10 mM Hepes pH 7.5, 100 mM NaCl. The dipegylated form was purified from other reaction products and free PEG by SP-Sepharose cation exchange chromatography at room temperature at a load concentration of 3 mg NBN/mL of resin. The column was washed with 4-one half column volume fractions of 10 mM Hepes pH 7.5, 150 mM NaCl, then the dipegylated product was eluted with 4-one half column volume fractions of 10 mM Hepes pH 7.5, 200 mM NaCl. Monopegylated NBN was then eluted with of 10 mM Hepes pH 7.5, 350 mM NaCl and unreacted NBN with of 10 mM Hepes pH 7.5, 800 mM NaCl. NBN-containing fractions were evaluated by SDS-PAGE and fractions containing >90% of the dipegylated product were pooled, dialyzed overnight against PBS and filtered through a 0.2 µm filter. Endotoxin levels were measured and were determined to be less than 1 EU/mg. The material was tested for function in the KIRA ELISA and neuronal survival assay and determined to be fully active. The final material was aliquoted and stored at −70C for subsequent testing. In early studies the monopegylated product was also collected for in vivo testing. However because of the better properties of the dipegylated material it was selected for all subsequent. To increase the yield of dipegylated material we further treated the monopegylated NBN with fresh PEG and again purified the dipegylated product from the reaction mix.

Example 3

Pharmacokinetics of PEGylated and Glycosylated Neublastin

The pharmacokinetic properties of PEGylated, gylcosylated neublastin in rat and mouse were examined. N-terminal PEGylation of glycosylated, truncated rat neublastin (N-terminus truncation of 9 amino acids; NBN104) with two 20,000 Da PEG moieties (2×20 KDa PEG NBN104) yielded a significant improvement in half-life and bioavailability of the neublastin. Following a 1.5 mg/kg subcutaneous administration to CD mice, serum levels of 97 ng/ml of PEGylated, glycosylated neublastin were detected at 24 hours. In contrast, following a 1.5 mg/kg subcutaneous administration of non-glycosylated NBN pegylated with two 20000 Da PEGs (2×20 KDa PEG) to mice, neublastin serum levels were 39 ng/ml at 24 hours. Neublastin was not detectable at 24 hours following a 1.5 mg/kg subcutaneous administration of unmodified glycosylated NBN104 to mice, indicating that serum levels of neublastin were less than 5 ng/ml. Surprisingly, the serum level achieved with the PEGylated, glycosylated neublastin was approximately 2.5-fold greater than the serum levels achieved with PEGylated, non-glycosylated neublastin.

Increased serum levels of N-terminus PEGylated, glycosylated neublastin were also observed in rat studies. Following a 1 mg/kg s.c. administration of 2 X 20 KDa PEG NBN104 to Sprague-Dawley rats, peak serum levels of 50 ng/ml of PEGylated neublastin were detected at 48 hours. Following a 1 mg/kg subcutanteous administration of non-PEGylated neublastin, serum levels at 48 hours were less than 2 ng/ml. These data indicated that N-terminal PEGylation of glycosylated neublastin (2 X 20 KDa PEG NBN104) resulted in peak serum levels of neublastin that were at least 19-fold greater than peak serum levels attained after administration of non-PEGylated, glycosylated neublastin. These data demonstrated that the combination of PEGylation at the N-terminus and glycosylation at amino acid 95 yielded a substantial enhancement of pharmacokinetic properties and bioavailability of neublastin.

Example 4

PEGgylated, Glycosylated Neublastin in Animal Model of Neuropathic Pain

The reversal effect of PEGylated, glycosylated neublastin on tactile allodynia and thermal hyperalgesia was studied in the Chung L5/L6 spinal nerve ligation ("SNL") model. Sprague-Dawley male rats (200-250 g) were divided into three groups. All rats received the spinal nerve ligation. One group of rats (n=6) was administered vehicle by subcutaneous injection. A second and third group of rats (n=6 per group) were administered 3 and 30 µg/kg PEGylated, glycosylated neublastin (2×20 KDa PEG NBN104) by subcutaneous injection, where the protein was CHO-derived, truncated (N-terminus truncation of 9 amino acids; NBN104), and PEGylated on each N-terminus with a 20,000 Da PEG. Since neublastin exists as a dimer, each dimer contains two 20,000 Da PEGs. The vehicle consisted of 5 mM phosphate and 150 mM sodium chloride at pH 6.5. Subcutaneous injections were administered on days 3, 5, 7, 10, 12 and 14 following the operation (post-SNL). The Von Frey and Hargreave's behavioral tests (Chaplan et al., 1994, *J. Neurosci. Meth.* 53:55-63; Hargreaves et al., 1988, *Pain* 32:77-88) were used to monitor tactile and thermal responses, respectively. These pain responses were monitored prior to the spinal nerve ligation to establish baseline responses, and then prior to drug administration on day 3 post-SNL, and approximately 1 hour following drug administration on days 5, 7, 10, 12 and 14 post-SNL. To assess statistical significance of drug treatment relative to vehicle treatment, a 2-way repeated measure analysis of variance (2-way RM ANOVA) was carried out followed by a post-hoc Student Neuman Keuls (SNK) test.

Figure 2:
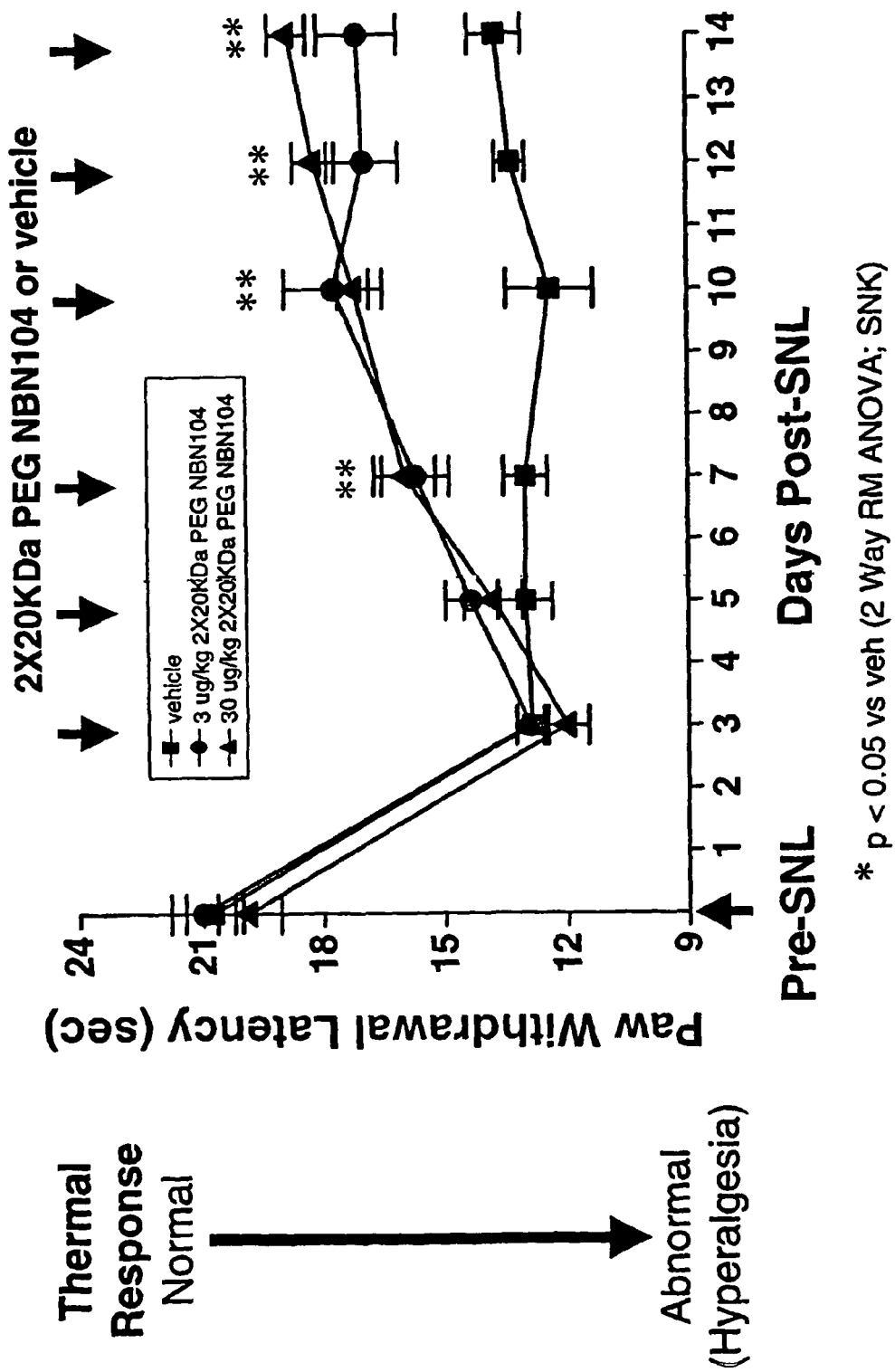
FIG. 2 is a broken line plot summarizing data showing substantial reversal of fully established thermal hyperalgesia by subcutaneous administration of 2×20 kDa PEG NBN104 in rats with L5/L6 spinal nerve ligation.

The results are summarized in FIGS. 1 and 2 (as averages±standard errors of the mean). Both types of neuropathic pain behavior (tactile allodynia shown in FIG. 1, and thermal hyperalgesia shown in FIG. 2) developed fully by day 3, as expected. Subcutaneous administration of 3 or 30 µg/kg 2×20 KDa PEG NBN104 (denoted by downward arrows in FIGS. 1 and 2) led to substantial and statistically significant reversal of both types of neuropathic pain in rats with spinal nerve ligation. In rats with spinal nerve ligation, the effect of 2×20 KDa PEG NBN104 on thermal sensitivity and tactile allodynia first became statistically significant 4 and 7 days, respectively, after the initiation of administration of pegylated glycosylated neublastin. The effect of 2×20 KDa PEG NBN1-4 on thermal sensitivity and tactile allodynia reached a plateau approximately 7 days after the initiation of administration of pegylated glycosylated neublastin. The effects of 2×20 KDa PEG NBN104 did not diminish during the 2 to 3 day interval between administrations. In fact, there was substantial normalization of pain behaviors between the administrations of pegylated glycosylated neublastin on days 5, 7 and 10.

These results demonstrated that 2×20 KDa PEG NBN104 has at least a 333-fold increased potency over non-PEGylated, non-glycosylated neublastin on tactile allodynia and thermal hyperalgesia pain behaviors in the SNL model.

Other Embodiments

Other embodiments are within the following claims.

What is claimed is:

1. A dimer comprising a first neublastin polypeptide and a second neublastin polypeptide, wherein: (a) at least one of the polypeptides is glycosylated; (b) at least one of the polypeptides is conjugated at its N-terminus to a water-soluble synthetic polymer; and (c) neither of the polypeptides is conjugated to a water-soluble synthetic polymer at a position other than the N-terminus.

2. The dimer according to claim 1, wherein the first neublastin polypeptide is selected from the group consisting of NBN113 (SEQ ID NO:2), NBN140 (SEQ ID NO:6), NBN116 (SEQ ID NO:7), NBN112 (SEQ ID NO:8), NBN111 (SEQ ID NO:9), NBN110 (SEQ ID NO:10), NBN109 (SEQ ID NO:11), NBN108 (SEQ ID NO:12), NBN107 (SEQ ID NO:13), NBN106 (SEQ ID NO:14), NBN105 (SEQ ID NO: 15), NBN104 (SEQ ID NO: 16), NBN103 (SEQ ID NO: 17), NBN102 (SEQ ID NO:18), NBN101 (SEQ ID NO:19), NBN100 (SEQ ID NO:20) and NBN99 (SEQ ID NO:21).

3. The dimer according to claim 1, wherein the amino acid sequence of the first neublastin polypeptide and the second neublastin polypeptide are the same.

4. The dimer of claim 3, wherein the amino acid sequence of the first neublastin polypeptide is NBN104 (SEQ ID NO:16).

5. The dimer of claim 1, wherein the water-soluble synthetic polymer is a polyalkylene glycol moiety.

6. The dimer of claim 5, wherein the N-terminal amino acid of the first neublastin polypeptide and the N-terminal amino acid of the second neublastin polypeptide each is conjugated to a polyalkylene glycol moiety.

7. The dimer according to claim 6, wherein the average total molecular weight of the polyalkylene glycol moiety or moieties conjugated to the dimer is 10-50 kDa.

8. The dimer of claim 7, wherein the average total molecular weight of the polyalkylene glycol moiety or moieties conjugated to the dimer is 15-45 kDa.

9. The dimer of claim 8, wherein the average total molecular weight of the polyalkylene glycol moiety or moieties conjugated to the dimer is 20-40 kDa.

10. The dimer according to claim 5, wherein the polyalkylene glycol moiety is linear.

11. The dimer according to claim 5, wherein the polyalkylene glycol is branched.

12. The dimer of claim 5, wherein the polyalkylene glycol moiety is a polyethylene glycol (PEG) moiety.

13. A composition comprising the dimer of claim 1 and a pharmaceutically acceptable carrier.

14. A method of treating neuropathic pain in a mammal, comprising administering to the mammal a therapeutically effective amount of the dimer of claim 1.

15. The method of claim 14, wherein the mammal is a human.

16. The method of claim 15, wherein the route of administration is intravenous, intramuscular or subcutaneous.

17. The method claim 14, wherein the therapeutically effective amount is from 0.1 µg/kg to 1000 µg/kg.

18. The method of claim 17, wherein the therapeutically effective amount is from 1 µg/kg to 100 µg/kg.

19. The method of claim 18, wherein the therapeutically effective amount is from 1 µg/kg to 30 µg/kg.

20. The method of claim 19, wherein the therapeutically effective amount is from 3 µg/kg to 10 µg/kg.

21. A method of treating tactile allodynia in a mammal, comprising administering to the mammal a therapeutically effective amount of the dimer of claim 1.

22. A method of treating thermal hyperalgesia, comprising administering to the mammal a therapeutically effective amount of the dimer of claim 1.

23. A method of activating the RET receptor in a mammal, comprising administering to the mammal an effective amount of the dimer of claim 1.

24. A method of treating neuropathic pain, tactile allodynia or thermal hyperalgesia in a mammal, comprising co-administering to the mammal an effective amount of the dimer of claim 1 and an analgesic agent.

25. A dimer comprising a first neublastin polypeptide and a second neublastin polypeptide, wherein: (a) at least one of the polypeptides is glycosylated; (b) at least one of the polypeptides is conjugated at its N-terminus to a polyethylene glycol moiety; and (c) neither of the polypeptides is conjugated to a polyethylene glycol moiety at a position other than the N-terminus, and wherein the amino acid sequence of the first neublastin polypeptide and the second neublastin is NBN104 (SEQ ID NO:16).

26. A composition comprising the dimer of claim 25 and a pharmaceutically acceptable carrier.

27. A method of treating neuropathic pain in a human, comprising administering to the human a therapeutically effective amount of the dimer of claim 25.

28. A method of activating the RET receptor in a human, comprising administering to the human an effective amount of the dimer of claim 25.

29. A method of treating a peripheral neuropathy in a human, comprising administering to the human a therapeutically effective amount of the dimer of claim 25.

30. A method of treating painful diabetic neuropathy in a human, comprising administering to the human a therapeutically effective amount of the dimer of claim 25.

31. The dimer of claim 25, wherein the N-terminal amino acid of the first neublastin polypeptide and the N-terminal amino acid of the second neublastin polypeptide each is conjugated to a polyethylene glycol moiety.

32. A composition comprising the dimer of claim 31 and a pharmaceutically acceptable carrier.

33. A method of treating neuropathic pain in a human, comprising administering to the human a therapeutically effective amount of the dimer of claim 31.

34. A method of activating the RET receptor in a human, comprising administering to the human an effective amount of the dimer of claim 31.

35. A method of treating a peripheral neuropathy in a human, comprising administering to the human a therapeutically effective amount of the dimer of claim 31.

36. A method of treating painful diabetic neuropathy in a human, comprising administering to the human a therapeutically effective amount of the dimer of claim 31.

37. A dimer comprising a first neublastin polypeptide and a second neublastin polypeptide, wherein: (a) at least one of the polypeptides is glycosylated; (b) at least one of the polypeptides is conjugated at its N-terminus to a polyethylene glycol moiety; and (c) neither of the polypeptides is conjugated to a polyethylene glycol moiety at a position other than the N-terminus, and wherein the amino acid sequence of the first neublastin polypeptide and the second neublastin is NBN113 (SEQ ID NO:2).

38. The dimer of claim 37, wherein the N-terminal amino acid of the first neublastin polypeptide and the N-terminal amino acid of the second neublastin polypeptide each is conjugated to a polyethylene glycol moiety.

39. A composition comprising the dimer of claim 37 and a pharmaceutically acceptable carrier.

40. A method of treating neuropathic pain in a human, comprising administering to the human a therapeutically effective amount of the dimer of claim 37.

41. A method of activating the RET receptor in a human, comprising administering to the human an effective amount of the dimer of claim 37.

42. A method of treating a peripheral neuropathy in a human, comprising administering to the human a therapeutically effective amount of the dimer of claim 37.

43. A method of treating painful diabetic neuropathy in a human, comprising administering to the human a therapeutically effective amount of the dimer of claim 37.

44. A composition comprising the dimer of claim 38 and a pharmaceutically acceptable carrier.

45. A method of treating neuropathic pain in a human, comprising administering to the human a therapeutically effective amount of the dimer of claim 38.

46. A method of activating the RET receptor in a human, comprising administering to the human an effective amount of the dimer of claim 38.

47. A method of treating a peripheral neuropathy in a human, comprising administering to the human a therapeutically effective amount of the dimer of claim 38.

48. A method of treating painful diabetic neuropathy in a human, comprising administering to the human a therapeutically effective amount of the dimer of claim 38.

* * * * *

UNITED STATES PATENT AND TRADEMARK OFFICE
CERTIFICATE OF CORRECTION

PATENT NO. : 8,163,875 B2
APPLICATION NO. : 10/553710
DATED : April 24, 2012
INVENTOR(S) : Dinah Wen-Yee Sah et al.

It is certified that error appears in the above-identified patent and that said Letters Patent is hereby corrected as shown below:

Title Page, Item (54), delete "POLYMER CONJUGATED" and insert
-- POLYMER-CONJUGATED --.

<u>Column 40</u>
Line 54, delete "method claim 14" and insert -- method of claim 14 --.

Signed and Sealed this
Tenth Day of July, 2012

David J. Kappos
*Director of the United States Patent and Trademark Office*

UNITED STATES PATENT AND TRADEMARK OFFICE
CERTIFICATE OF CORRECTION

PATENT NO. : 8,163,875 B2
APPLICATION NO. : 10/553710
DATED : April 24, 2012
INVENTOR(S) : Dinah Wen-Yee Sah et al.

It is certified that error appears in the above-identified patent and that said Letters Patent is hereby corrected as shown below:

Title Page, Item (54) and Column 1, lines 1 and 2, Title, delete "POLYMER CONJUGATED" and insert -- POLYMER-CONJUGATED --.

Column 40
Line 54, delete "method claim 14" and insert -- method of claim 14 --.

This certificate supersedes the Certificate of Correction issued July 10, 2012.

Signed and Sealed this
Fourteenth Day of August, 2012

David J. Kappos
*Director of the United States Patent and Trademark Office*

```
                            SEQUENCE LISTING

<160> NUMBER OF SEQ ID NOS: 37

<210> SEQ ID NO 1
<211> LENGTH: 113
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 3
<223> OTHER INFORMATION: Xaa = Gly or Thr
<220> FEATURE:
<221> NAME/KEY: VARIANT
<222> LOCATION: 4
<223> OTHER INFORMATION: Xaa = Pro or Arg
<220> FEATURE:
<221> NAME/KEY: VARIANT
<222> LOCATION: 5
<223> OTHER INFORMATION: Xaa = Gly or Ser
<220> FEATURE:
<221> NAME/KEY: VARIANT
<222> LOCATION: 10, 11
<223> OTHER INFORMATION: Xaa = Ala or Thr
<220> FEATURE:
<221> NAME/KEY: VARIANT
<222> LOCATION: 12
<223> OTHER INFORMATION: Xaa = Gly or Asp
<220> FEATURE:
<221> NAME/KEY: VARIANT
<222> LOCATION: 26, 33
<223> OTHER INFORMATION: Xaa = Arg or Ser
<220> FEATURE:
<221> NAME/KEY: VARIANT
<222> LOCATION: 38, 76
<223> OTHER INFORMATION: Xaa = Val or Ile
<220> FEATURE:
<221> NAME/KEY: VARIANT
<222> LOCATION: 53
<223> OTHER INFORMATION: Xaa = Pro or Gln
<220> FEATURE:
<221> NAME/KEY: VARIANT
<222> LOCATION: 69
<223> OTHER INFORMATION: Xaa = Pro or Ser
<220> FEATURE:
<221> NAME/KEY: VARIANT
<222> LOCATION: 103
<223> OTHER INFORMATION: Xaa = Arg or His

<400> SEQUENCE: 1

Ala Gly Xaa Xaa Xaa Ser Arg Ala Arg Xaa Xaa Xaa Ala Arg Gly Cys
1               5                   10                  15

Arg Leu Arg Ser Gln Leu Val Pro Val Xaa Ala Leu Gly Leu Gly His
            20                  25                  30

Xaa Ser Asp Glu Leu Xaa Arg Phe Arg Phe Cys Ser Gly Ser Cys Arg
        35                  40                  45

Arg Ala Arg Ser Xaa His Asp Leu Ser Leu Ala Ser Leu Leu Gly Ala
```

```
                50                  55                  60
Gly Ala Leu Arg Xaa Pro Pro Gly Ser Arg Pro Xaa Ser Gln Pro Cys
 65                  70                  75                  80

Cys Arg Pro Thr Arg Tyr Glu Ala Val Ser Phe Met Asp Val Asn Ser
                 85                  90                  95

Thr Trp Arg Thr Val Asp Xaa Leu Ser Ala Thr Ala Cys Gly Cys Leu
                100                 105                 110

Gly

<210> SEQ ID NO 2
<211> LENGTH: 113
<212> TYPE: PRT
<213> ORGANISM: Homo sapiens

<400> SEQUENCE: 2

Ala Gly Gly Pro Gly Ser Arg Ala Arg Ala Ala Gly Ala Arg Gly Cys
  1               5                  10                  15

Arg Leu Arg Ser Gln Leu Val Pro Val Arg Ala Leu Gly Leu Gly His
                 20                  25                  30

Arg Ser Asp Glu Leu Val Arg Phe Arg Phe Cys Ser Gly Ser Cys Arg
                 35                  40                  45

Arg Ala Arg Ser Pro His Asp Leu Ser Leu Ala Ser Leu Leu Gly Ala
             50                  55                  60

Gly Ala Leu Arg Pro Pro Gly Ser Arg Pro Val Ser Gln Pro Cys
 65                  70                  75                  80

Cys Arg Pro Thr Arg Tyr Glu Ala Val Ser Phe Met Asp Val Asn Ser
                 85                  90                  95

Thr Trp Arg Thr Val Asp Arg Leu Ser Ala Thr Ala Cys Gly Cys Leu
                100                 105                 110

Gly

<210> SEQ ID NO 3
<211> LENGTH: 113
<212> TYPE: PRT
<213> ORGANISM: Mus musculus

<400> SEQUENCE: 3

Ala Gly Thr Arg Ser Ser Arg Ala Arg Thr Thr Asp Ala Arg Gly Cys
  1               5                  10                  15

Arg Leu Arg Ser Gln Leu Val Pro Val Ser Ala Leu Gly Leu Gly His
                 20                  25                  30

Ser Ser Asp Glu Leu Ile Arg Phe Arg Phe Cys Ser Gly Ser Cys Arg
                 35                  40                  45

Arg Ala Arg Ser Gln His Asp Leu Ser Leu Ala Ser Leu Leu Gly Ala
             50                  55                  60

Gly Ala Leu Arg Ser Pro Gly Ser Arg Pro Ile Ser Gln Pro Cys
 65                  70                  75                  80

Cys Arg Pro Thr Arg Tyr Glu Ala Val Ser Phe Met Asp Val Asn Ser
                 85                  90                  95

Thr Trp Arg Thr Val Asp His Leu Ser Ala Thr Ala Cys Gly Cys Leu
                100                 105                 110

Gly

<210> SEQ ID NO 4
<211> LENGTH: 113
<212> TYPE: PRT
<213> ORGANISM: Rattus norvegicus
```

-continued

<400> SEQUENCE: 4

```
Ala Gly Thr Arg Ser Ser Arg Ala Arg Ala Thr Asp Ala Arg Gly Cys
 1               5                  10                  15

Arg Leu Arg Ser Gln Leu Val Pro Val Ser Ala Leu Gly Leu Gly His
            20                  25                  30

Ser Ser Asp Glu Leu Ile Arg Phe Arg Phe Cys Ser Gly Ser Cys Arg
        35                  40                  45

Arg Ala Arg Ser Pro His Asp Leu Ser Leu Ala Ser Leu Leu Gly Ala
    50                  55                  60

Gly Ala Leu Arg Ser Pro Gly Ser Arg Pro Ile Ser Gln Pro Cys
 65                 70                  75                  80

Cys Arg Pro Thr Arg Tyr Glu Ala Val Ser Phe Met Asp Val Asn Ser
                85                  90                  95

Thr Trp Arg Thr Val Asp His Leu Ser Ala Thr Ala Cys Gly Cys Leu
               100                 105                 110

Gly
```

<210> SEQ ID NO 5
<211> LENGTH: 220
<212> TYPE: PRT
<213> ORGANISM: Homo sapiens

<400> SEQUENCE: 5

```
Met Glu Leu Gly Leu Gly Gly Leu Ser Thr Leu Ser His Cys Pro Trp
 1               5                  10                  15

Pro Arg Arg Gln Pro Ala Leu Trp Pro Thr Leu Ala Ala Leu Ala Leu
            20                  25                  30

Leu Ser Ser Val Ala Glu Ala Ser Leu Gly Ser Ala Pro Arg Ser Pro
        35                  40                  45

Ala Pro Arg Glu Gly Pro Pro Val Leu Ala Ser Pro Ala Gly His
    50                  55                  60

Leu Pro Gly Gly Arg Thr Ala Arg Trp Cys Ser Gly Arg Ala Arg Arg
 65                 70                  75                  80

Pro Pro Gln Pro Ser Arg Pro Ala Pro Pro Ala Pro Pro
                85                  90                  95

Ser Ala Leu Pro Arg Gly Gly Arg Ala Ala Arg Ala Gly Gly Pro Gly
               100                 105                 110

Ser Arg Ala Arg Ala Ala Gly Ala Arg Gly Cys Arg Leu Arg Ser Gln
               115                 120                 125

Leu Val Pro Val Arg Ala Leu Gly Leu Gly His Arg Ser Asp Glu Leu
130                 135                 140

Val Arg Phe Arg Phe Cys Ser Gly Ser Cys Arg Arg Ala Arg Ser Pro
145                 150                 155                 160

His Asp Leu Ser Leu Ala Ser Leu Leu Gly Ala Gly Ala Leu Arg Pro
               165                 170                 175

Pro Pro Gly Ser Arg Pro Val Ser Gln Pro Cys Cys Arg Pro Thr Arg
               180                 185                 190

Tyr Glu Ala Val Ser Phe Met Asp Val Asn Ser Thr Trp Arg Thr Val
               195                 200                 205

Asp Arg Leu Ser Ala Thr Ala Cys Gly Cys Leu Gly
               210                 215                 220
```

<210> SEQ ID NO 6
<211> LENGTH: 140
<212> TYPE: PRT

<213> ORGANISM: Homo sapiens

<400> SEQUENCE: 6

Pro Pro Pro Gln Pro Ser Arg Pro Ala Pro Pro Pro Ala Pro Pro
1               5                   10                  15

Ser Ala Leu Pro Arg Gly Gly Arg Ala Arg Ala Gly Gly Pro Gly
            20                  25                  30

Ser Arg Ala Arg Ala Ala Gly Ala Arg Gly Cys Arg Leu Arg Ser Gln
            35                  40                  45

Leu Val Pro Val Arg Ala Leu Gly Leu Gly His Arg Ser Asp Glu Leu
        50                  55                  60

Val Arg Phe Arg Phe Cys Ser Gly Ser Cys Arg Arg Ala Arg Ser Pro
65                  70                  75                  80

His Asp Leu Ser Leu Ala Ser Leu Leu Gly Ala Gly Ala Leu Arg Pro
                85                  90                  95

Pro Pro Gly Ser Arg Pro Val Ser Gln Pro Cys Cys Arg Pro Thr Arg
            100                 105                 110

Tyr Glu Ala Val Ser Phe Met Asp Val Asn Ser Thr Trp Arg Thr Val
            115                 120                 125

Asp Arg Leu Ser Ala Thr Ala Cys Gly Cys Leu Gly
            130                 135                 140

<210> SEQ ID NO 7
<211> LENGTH: 116
<212> TYPE: PRT
<213> ORGANISM: Homo sapiens

<400> SEQUENCE: 7

Ala Ala Arg Ala Gly Gly Pro Gly Ser Arg Ala Arg Ala Ala Gly Ala
1               5                   10                  15

Arg Gly Cys Arg Leu Arg Ser Gln Leu Val Pro Val Arg Ala Leu Gly
            20                  25                  30

Leu Gly His Arg Ser Asp Glu Leu Val Arg Phe Arg Phe Cys Ser Gly
        35                  40                  45

Ser Cys Arg Arg Ala Arg Ser Pro His Asp Leu Ser Leu Ala Ser Leu
    50                  55                  60

Leu Gly Ala Gly Ala Leu Arg Pro Pro Pro Gly Ser Arg Pro Val Ser
65                  70                  75                  80

Gln Pro Cys Cys Arg Pro Thr Arg Tyr Glu Ala Val Ser Phe Met Asp
                85                  90                  95

Val Asn Ser Thr Trp Arg Thr Val Asp Arg Leu Ser Ala Thr Ala Cys
            100                 105                 110

Gly Cys Leu Gly
        115

<210> SEQ ID NO 8
<211> LENGTH: 112
<212> TYPE: PRT
<213> ORGANISM: Homo sapiens

<400> SEQUENCE: 8

Gly Gly Pro Gly Ser Arg Ala Arg Ala Ala Gly Ala Arg Gly Cys Arg
1               5                   10                  15

Leu Arg Ser Gln Leu Val Pro Val Arg Ala Leu Gly Leu Gly His Arg
            20                  25                  30

Ser Asp Glu Leu Val Arg Phe Arg Phe Cys Ser Gly Ser Cys Arg Arg
        35                  40                  45

Ala Arg Ser Pro His Asp Leu Ser Leu Ala Ser Leu Leu Gly Ala Gly
    50                  55                  60

Ala Leu Arg Pro Pro Gly Ser Arg Pro Val Ser Gln Pro Cys Cys
65                  70                  75                  80

Arg Pro Thr Arg Tyr Glu Ala Val Ser Phe Met Asp Val Asn Ser Thr
                85                  90                  95

Trp Arg Thr Val Asp Arg Leu Ser Ala Thr Ala Cys Gly Cys Leu Gly
            100                 105                 110

<210> SEQ ID NO 9
<211> LENGTH: 111
<212> TYPE: PRT
<213> ORGANISM: Homo sapiens

<400> SEQUENCE: 9

Gly Pro Gly Ser Arg Ala Arg Ala Ala Gly Ala Arg Gly Cys Arg Leu
1               5                   10                  15

Arg Ser Gln Leu Val Pro Val Arg Ala Leu Gly Leu Gly His Arg Ser
                20                  25                  30

Asp Glu Leu Val Arg Phe Arg Phe Cys Ser Gly Ser Cys Arg Arg Ala
            35                  40                  45

Arg Ser Pro His Asp Leu Ser Leu Ala Ser Leu Leu Gly Ala Gly Ala
        50                  55                  60

Leu Arg Pro Pro Pro Gly Ser Arg Pro Val Ser Gln Pro Cys Cys Arg
65                  70                  75                  80

Pro Thr Arg Tyr Glu Ala Val Ser Phe Met Asp Val Asn Ser Thr Trp
                85                  90                  95

Arg Thr Val Asp Arg Leu Ser Ala Thr Ala Cys Gly Cys Leu Gly
            100                 105                 110

<210> SEQ ID NO 10
<211> LENGTH: 110
<212> TYPE: PRT
<213> ORGANISM: Homo sapiens

<400> SEQUENCE: 10

Pro Gly Ser Arg Ala Arg Ala Ala Gly Ala Arg Gly Cys Arg Leu Arg
1               5                   10                  15

Ser Gln Leu Val Pro Val Arg Ala Leu Gly Leu Gly His Arg Ser Asp
                20                  25                  30

Glu Leu Val Arg Phe Arg Phe Cys Ser Gly Ser Cys Arg Arg Ala Arg
            35                  40                  45

Ser Pro His Asp Leu Ser Leu Ala Ser Leu Leu Gly Ala Gly Ala Leu
        50                  55                  60

Arg Pro Pro Pro Gly Ser Arg Pro Val Ser Gln Pro Cys Cys Arg Pro
65                  70                  75                  80

Thr Arg Tyr Glu Ala Val Ser Phe Met Asp Val Asn Ser Thr Trp Arg
                85                  90                  95

Thr Val Asp Arg Leu Ser Ala Thr Ala Cys Gly Cys Leu Gly
            100                 105                 110

<210> SEQ ID NO 11
<211> LENGTH: 109
<212> TYPE: PRT
<213> ORGANISM: Homo sapiens

<400> SEQUENCE: 11

Gly Ser Arg Ala Arg Ala Ala Gly Ala Arg Gly Cys Arg Leu Arg Ser
1               5                   10                  15

```
Gln Leu Val Pro Val Arg Ala Leu Gly Leu Gly His Arg Ser Asp Glu
             20                  25                  30

Leu Val Arg Phe Arg Phe Cys Ser Gly Ser Cys Arg Arg Ala Arg Ser
         35                  40                  45

Pro His Asp Leu Ser Leu Ala Ser Leu Leu Gly Ala Gly Ala Leu Arg
     50                  55                  60

Pro Pro Pro Gly Ser Arg Pro Val Ser Gln Pro Cys Cys Arg Pro Thr
 65                  70                  75                  80

Arg Tyr Glu Ala Val Ser Phe Met Asp Val Asn Ser Thr Trp Arg Thr
                 85                  90                  95

Val Asp Arg Leu Ser Ala Thr Ala Cys Gly Cys Leu Gly
             100                 105
```

<210> SEQ ID NO 12
<211> LENGTH: 108
<212> TYPE: PRT
<213> ORGANISM: Homo sapiens

<400> SEQUENCE: 12

```
Ser Arg Ala Arg Ala Ala Gly Ala Arg Gly Cys Arg Leu Arg Ser Gln
 1               5                  10                  15

Leu Val Pro Val Arg Ala Leu Gly Leu Gly His Arg Ser Asp Glu Leu
             20                  25                  30

Val Arg Phe Arg Phe Cys Ser Gly Ser Cys Arg Arg Ala Arg Ser Pro
         35                  40                  45

His Asp Leu Ser Leu Ala Ser Leu Leu Gly Ala Gly Ala Leu Arg Pro
     50                  55                  60

Pro Pro Gly Ser Arg Pro Val Ser Gln Pro Cys Cys Arg Pro Thr Arg
 65                  70                  75                  80

Tyr Glu Ala Val Ser Phe Met Asp Val Asn Ser Thr Trp Arg Thr Val
                 85                  90                  95

Asp Arg Leu Ser Ala Thr Ala Cys Gly Cys Leu Gly
             100                 105
```

<210> SEQ ID NO 13
<211> LENGTH: 107
<212> TYPE: PRT
<213> ORGANISM: Homo sapiens

<400> SEQUENCE: 13

```
Arg Ala Arg Ala Ala Gly Ala Arg Gly Cys Arg Leu Arg Ser Gln Leu
 1               5                  10                  15

Val Pro Val Arg Ala Leu Gly Leu Gly His Arg Ser Asp Glu Leu Val
             20                  25                  30

Arg Phe Arg Phe Cys Ser Gly Ser Cys Arg Arg Ala Arg Ser Pro His
         35                  40                  45

Asp Leu Ser Leu Ala Ser Leu Leu Gly Ala Gly Ala Leu Arg Pro Pro
     50                  55                  60

Pro Gly Ser Arg Pro Val Ser Gln Pro Cys Cys Arg Pro Thr Arg Tyr
 65                  70                  75                  80

Glu Ala Val Ser Phe Met Asp Val Asn Ser Thr Trp Arg Thr Val Asp
                 85                  90                  95

Arg Leu Ser Ala Thr Ala Cys Gly Cys Leu Gly
             100                 105
```

<210> SEQ ID NO 14
<211> LENGTH: 106

```
<212> TYPE: PRT
<213> ORGANISM: Homo sapiens

<400> SEQUENCE: 14

Ala Arg Ala Ala Gly Ala Arg Gly Cys Arg Leu Arg Ser Gln Leu Val
 1               5                  10                  15

Pro Val Arg Ala Leu Gly Leu Gly His Arg Ser Asp Glu Leu Val Arg
             20                  25                  30

Phe Arg Phe Cys Ser Gly Ser Cys Arg Arg Ala Arg Ser Pro His Asp
         35                  40                  45

Leu Ser Leu Ala Ser Leu Leu Gly Ala Gly Ala Leu Arg Pro Pro Pro
     50                  55                  60

Gly Ser Arg Pro Val Ser Gln Pro Cys Cys Arg Pro Thr Arg Tyr Glu
 65                  70                  75                  80

Ala Val Ser Phe Met Asp Val Asn Ser Thr Trp Arg Thr Val Asp Arg
                 85                  90                  95

Leu Ser Ala Thr Ala Cys Gly Cys Leu Gly
                100                 105

<210> SEQ ID NO 15
<211> LENGTH: 105
<212> TYPE: PRT
<213> ORGANISM: Homo sapiens

<400> SEQUENCE: 15

Arg Ala Ala Gly Ala Arg Gly Cys Arg Leu Arg Ser Gln Leu Val Pro
 1               5                  10                  15

Val Arg Ala Leu Gly Leu Gly His Arg Ser Asp Glu Leu Val Arg Phe
             20                  25                  30

Arg Phe Cys Ser Gly Ser Cys Arg Arg Ala Arg Ser Pro His Asp Leu
         35                  40                  45

Ser Leu Ala Ser Leu Leu Gly Ala Gly Ala Leu Arg Pro Pro Pro Gly
     50                  55                  60

Ser Arg Pro Val Ser Gln Pro Cys Cys Arg Pro Thr Arg Tyr Glu Ala
 65                  70                  75                  80

Val Ser Phe Met Asp Val Asn Ser Thr Trp Arg Thr Val Asp Arg Leu
                 85                  90                  95

Ser Ala Thr Ala Cys Gly Cys Leu Gly
                100                 105

<210> SEQ ID NO 16
<211> LENGTH: 104
<212> TYPE: PRT
<213> ORGANISM: Homo sapiens

<400> SEQUENCE: 16

Ala Ala Gly Ala Arg Gly Cys Arg Leu Arg Ser Gln Leu Val Pro Val
 1               5                  10                  15

Arg Ala Leu Gly Leu Gly His Arg Ser Asp Glu Leu Val Arg Phe Arg
             20                  25                  30

Phe Cys Ser Gly Ser Cys Arg Arg Ala Arg Ser Pro His Asp Leu Ser
         35                  40                  45

Leu Ala Ser Leu Leu Gly Ala Gly Ala Leu Arg Pro Pro Pro Gly Ser
     50                  55                  60

Arg Pro Val Ser Gln Pro Cys Cys Arg Pro Thr Arg Tyr Glu Ala Val
 65                  70                  75                  80

Ser Phe Met Asp Val Asn Ser Thr Trp Arg Thr Val Asp Arg Leu Ser
                 85                  90                  95
```

```
Ala Thr Ala Cys Gly Cys Leu Gly
            100

<210> SEQ ID NO 17
<211> LENGTH: 103
<212> TYPE: PRT
<213> ORGANISM: Homo sapiens

<400> SEQUENCE: 17

Ala Gly Ala Arg Gly Cys Arg Leu Arg Ser Gln Leu Val Pro Val Arg
1               5                   10                  15

Ala Leu Gly Leu Gly His Arg Ser Asp Glu Leu Val Arg Phe Arg Phe
            20                  25                  30

Cys Ser Gly Ser Cys Arg Arg Ala Arg Ser Pro His Asp Leu Ser Leu
        35                  40                  45

Ala Ser Leu Leu Gly Ala Gly Ala Leu Arg Pro Pro Pro Gly Ser Arg
    50                  55                  60

Pro Val Ser Gln Pro Cys Cys Arg Pro Thr Arg Tyr Glu Ala Val Ser
65                  70                  75                  80

Phe Met Asp Val Asn Ser Thr Trp Arg Thr Val Asp Arg Leu Ser Ala
                85                  90                  95

Thr Ala Cys Gly Cys Leu Gly
            100

<210> SEQ ID NO 18
<211> LENGTH: 102
<212> TYPE: PRT
<213> ORGANISM: Homo sapiens

<400> SEQUENCE: 18

Gly Ala Arg Gly Cys Arg Leu Arg Ser Gln Leu Val Pro Val Arg Ala
1               5                   10                  15

Leu Gly Leu Gly His Arg Ser Asp Glu Leu Val Arg Phe Arg Phe Cys
            20                  25                  30

Ser Gly Ser Cys Arg Arg Ala Arg Ser Pro His Asp Leu Ser Leu Ala
        35                  40                  45

Ser Leu Leu Gly Ala Gly Ala Leu Arg Pro Pro Pro Gly Ser Arg Pro
    50                  55                  60

Val Ser Gln Pro Cys Cys Arg Pro Thr Arg Tyr Glu Ala Val Ser Phe
65                  70                  75                  80

Met Asp Val Asn Ser Thr Trp Arg Thr Val Asp Arg Leu Ser Ala Thr
                85                  90                  95

Ala Cys Gly Cys Leu Gly
            100

<210> SEQ ID NO 19
<211> LENGTH: 101
<212> TYPE: PRT
<213> ORGANISM: Homo sapiens

<400> SEQUENCE: 19

Ala Arg Gly Cys Arg Leu Arg Ser Gln Leu Val Pro Val Arg Ala Leu
1               5                   10                  15

Gly Leu Gly His Arg Ser Asp Glu Leu Val Arg Phe Arg Phe Cys Ser
            20                  25                  30

Gly Ser Cys Arg Arg Ala Arg Ser Pro His Asp Leu Ser Leu Ala Ser
        35                  40                  45

Leu Leu Gly Ala Gly Ala Leu Arg Pro Pro Pro Gly Ser Arg Pro Val
```

```
                    50                  55                  60
Ser Gln Pro Cys Cys Arg Pro Thr Arg Tyr Glu Ala Val Ser Phe Met
 65                  70                  75                  80

Asp Val Asn Ser Thr Trp Arg Thr Val Asp Arg Leu Ser Ala Thr Ala
                 85                  90                  95

Cys Gly Cys Leu Gly
            100

<210> SEQ ID NO 20
<211> LENGTH: 100
<212> TYPE: PRT
<213> ORGANISM: Homo sapiens

<400> SEQUENCE: 20

Arg Gly Cys Arg Leu Arg Ser Gln Leu Val Pro Val Arg Ala Leu Gly
 1               5                  10                  15

Leu Gly His Arg Ser Asp Glu Leu Val Arg Phe Arg Phe Cys Ser Gly
                 20                  25                  30

Ser Cys Arg Arg Ala Arg Ser Pro His Asp Leu Ser Leu Ala Ser Leu
             35                  40                  45

Leu Gly Ala Gly Ala Leu Arg Pro Pro Pro Gly Ser Arg Pro Val Ser
 50                  55                  60

Gln Pro Cys Cys Arg Pro Thr Arg Tyr Glu Ala Val Ser Phe Met Asp
 65                  70                  75                  80

Val Asn Ser Thr Trp Arg Thr Val Asp Arg Leu Ser Ala Thr Ala Cys
                 85                  90                  95

Gly Cys Leu Gly
            100

<210> SEQ ID NO 21
<211> LENGTH: 99
<212> TYPE: PRT
<213> ORGANISM: Homo sapiens

<400> SEQUENCE: 21

Gly Cys Arg Leu Arg Ser Gln Leu Val Pro Val Arg Ala Leu Gly Leu
 1               5                  10                  15

Gly His Arg Ser Asp Glu Leu Val Arg Phe Arg Phe Cys Ser Gly Ser
                 20                  25                  30

Cys Arg Arg Ala Arg Ser Pro His Asp Leu Ser Leu Ala Ser Leu Leu
             35                  40                  45

Gly Ala Gly Ala Leu Arg Pro Pro Pro Gly Ser Arg Pro Val Ser Gln
 50                  55                  60

Pro Cys Cys Arg Pro Thr Arg Tyr Glu Ala Val Ser Phe Met Asp Val
 65                  70                  75                  80

Asn Ser Thr Trp Arg Thr Val Asp Arg Leu Ser Ala Thr Ala Cys Gly
                 85                  90                  95

Cys Leu Gly

<210> SEQ ID NO 22
<211> LENGTH: 39
<212> TYPE: DNA
<213> ORGANISM: Artificial Sequence
<220> FEATURE:
<223> OTHER INFORMATION: oligonucleotide for PCR

<400> SEQUENCE: 22
aaggaaaaaa gcggccgcca tggaacttgg acttggagg                    39
```

```
<210> SEQ ID NO 23
<211> LENGTH: 39
<212> TYPE: DNA
<213> ORGANISM: Artificial Sequence
<220> FEATURE:
<223> OTHER INFORMATION: oligonucleotide for PCR

<400> SEQUENCE: 23
tttttccctt ggcggccgct cagcccaggc agccgcagg                              39

<210> SEQ ID NO 24
<211> LENGTH: 24
<212> TYPE: PRT
<213> ORGANISM: Rattus norvegicus

<400> SEQUENCE: 24

Met Lys Trp Val Thr Phe Leu Leu Leu Phe Ile Ser Gly Ser Ala
 1               5                  10                  15

Phe Ser Ala Ala Gly Ala Arg Gly
                 20

<210> SEQ ID NO 25
<211> LENGTH: 32
<212> TYPE: PRT
<213> ORGANISM: Homo sapiens

<400> SEQUENCE: 25

Met Ala Thr Gly Ser Arg Thr Ser Leu Leu Leu Ala Phe Gly Leu Leu
 1               5                  10                  15

Cys Leu Ser Trp Leu Gln Glu Gly Ser Ala Ala Ala Gly Ala Arg Gly
                 20                  25                  30

<210> SEQ ID NO 26
<211> LENGTH: 23
<212> TYPE: DNA
<213> ORGANISM: Artificial Sequence
<220> FEATURE:
<223> OTHER INFORMATION: oligonucleotide for PCR

<400> SEQUENCE: 26
actcactata gggctcgagc ggc                                              23

<210> SEQ ID NO 27
<211> LENGTH: 27
<212> TYPE: DNA
<213> ORGANISM: Artificial Sequence
<220> FEATURE:
<223> OTHER INFORMATION: oligonucleotide for PCR

<400> SEQUENCE: 27
gaaccgctgc agaagcggaa acgtatc                                          27

<210> SEQ ID NO 28
<211> LENGTH: 39
<212> TYPE: DNA
<213> ORGANISM: Artificial Sequence
<220> FEATURE:
<223> OTHER INFORMATION: oligonucleotide for PCR

<400> SEQUENCE: 28
aaggaaaaaa gcggccgcca tgaactgggg acttggaga                             39

<210> SEQ ID NO 29
<211> LENGTH: 40
<212> TYPE: DNA
```

<213> ORGANISM: Artificial Sequence
<220> FEATURE:
<223> OTHER INFORMATION: oligonucleotide for PCR

<400> SEQUENCE: 29
agttcgtcgg aagagtgtcc caggccgaga gcgctcaccg                             40

<210> SEQ ID NO 30
<211> LENGTH: 40
<212> TYPE: DNA
<213> ORGANISM: Artificial Sequence
<220> FEATURE:
<223> OTHER INFORMATION: oligonucleotide for PCR

<400> SEQUENCE: 30
cggtgagcgc tctcggcctg ggacactctt ccgacgaact                             40

<210> SEQ ID NO 31
<211> LENGTH: 39
<212> TYPE: DNA
<213> ORGANISM: Artificial Sequence
<220> FEATURE:
<223> OTHER INFORMATION: oligonucleotide for PCR

<400> SEQUENCE: 31
tttttccctt ggcggccgct catcctagac agccacatg                              39

<210> SEQ ID NO 32
<211> LENGTH: 387
<212> TYPE: DNA
<213> ORGANISM: Rattus norvegicus

<400> SEQUENCE: 32
gctcgagcgg ccatatcgac gacgacgaca aggctggaac tcgcagctct cgtgctcgtg        60
caaccgatgc acgtggctgt cgtctgcgtt ctcaactagt gccggtgtct gcactcggac       120
tgggacactc ttccgacgaa ctaattcgtt ttcgttttg ttcaggatct tgtcgtcgtg        180
cacgttctcc gcatgatcta tctctagcat ctctactagg agccggagca ctaagatctc       240
cgccgggatc tagacctatt tctcaacctt gttgtagacc tactagatac gaagcagtat       300
ctttcatgga cgtaaactct acatggagaa ccgtagatca tctatctgca accgcatgtg       360
gctgtctagg atgataatag ggatccg                                          387

<210> SEQ ID NO 33
<211> LENGTH: 4
<212> TYPE: PRT
<213> ORGANISM: Artificial Sequence
<220> FEATURE:
<223> OTHER INFORMATION: exemplary motif

<400> SEQUENCE: 33

Leu Gly Leu Gly
  1

<210> SEQ ID NO 34
<211> LENGTH: 4
<212> TYPE: PRT
<213> ORGANISM: Artificial Sequence
<220> FEATURE:
<223> OTHER INFORMATION: exemplary motif

<400> SEQUENCE: 34

Phe Arg Phe Cys
  1

```
<210> SEQ ID NO 35
<211> LENGTH: 6
<212> TYPE: PRT
<213> ORGANISM: Artificial Sequence
<220> FEATURE:
<223> OTHER INFORMATION: exemplary motif

<400> SEQUENCE: 35

Gln Pro Cys Cys Arg Pro
 1               5

<210> SEQ ID NO 36
<211> LENGTH: 7
<212> TYPE: PRT
<213> ORGANISM: Artificial Sequence
<220> FEATURE:
<223> OTHER INFORMATION: exemplary motif

<400> SEQUENCE: 36

Ser Ala Thr Ala Cys Gly Cys
 1               5

<210> SEQ ID NO 37
<211> LENGTH: 7
<212> TYPE: PRT
<213> ORGANISM: Homo sapiens

<400> SEQUENCE: 37

Ala Thr Asp Ala Arg Gly Cys
 1               5
```

UNITED STATES PATENT AND TRADEMARK OFFICE
CERTIFICATE OF CORRECTION

PATENT NO. : 8,163,875 B2  
APPLICATION NO. : 10/553710  
DATED : April 24, 2012  
INVENTOR(S) : Sah et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1449 days.

Signed and Sealed this  
Seventeenth Day of March, 2020

Andrei Iancu  
*Director of the United States Patent and Trademark Office*